United States Patent [19]

Fukuoka et al.

[11] Patent Number: 5,210,268
[45] Date of Patent: May 11, 1993

[54] PROCESS FOR CONTINUOUSLY PRODUCING AN AROMATIC CARBONATE

[75] Inventors: Shinsuke Fukuoka; Masahiro Tojo, both of Kurashiki; Mamoru Kawamura, Omiya, all of Japan

[73] Assignee: Asahi Kasei Kogyo Kabushiki Kaisha, Osaka, Japan

[21] Appl. No.: 688,588

[22] PCT Filed: Dec. 28, 1990

[86] PCT No.: PCT/JP90/01734

§ 371 Date: Jun. 28, 1991

§ 102(e) Date: Jun. 28, 1991

[87] PCT Pub. No.: WO91/09832

PCT Pub. Date: Jul. 11, 1991

[30] Foreign Application Priority Data

Dec. 28, 1989 [JP] Japan .................................. 1-338179
Dec. 28, 1989 [JP] Japan .................................. 1-338180
Feb. 21, 1990 [JP] Japan .................................. 2-38436

[51] Int. Cl.$^5$ .............................................. C07C 69/96
[52] U.S. Cl. .................................. 558/270; 558/274; 558/277
[58] Field of Search .......................... 558/270, 274, 277

[56] References Cited

U.S. PATENT DOCUMENTS 4,252,737 2/1981 Krimm et al. ........................ 260/463

FOREIGN PATENT DOCUMENTS 1-265063 10/1989 Japan .
1-265064 10/1989 Japan .

OTHER PUBLICATIONS

Chemical Abstract 106:195891d, Jun. 1987.
Chemical Abstract 90:186578f, Jun. 1979.
Chemical Abstract 91:92272y, Sep. 1979.
Chemical Abstract 109:210720e, Dec. 1988.
Chemical Abstract 95:80505t, Aug. 1981.
Chemical Abstract 98:125616k, Apr. 1983.
Chemical Abstract 98:106994r, Mar. 1983.
Chemical Abstract 106:67825y, Mar. 1987.
Chemical Abstract 111:133766m, Oct. 1989.
Chemical Abstract 112:157845h, Apr. 1990.
Chemical Abstract 92:58427k, Feb. 1980.

*Primary Examiner*—Jose G. Dees
*Assistant Examiner*—Porfirio Nazario
*Attorney, Agent, or Firm*—Birch, Stewart, Kolasch & Birch

[57] ABSTRACT

Disclosed is a process for producing an aromatic carbonate or aromatic carbonate mixture by a transesterification reaction between a starting material selected from a dialkyl carbonate, an alkyl aryl carbonate and a mixture thereof and a reactant selected from an aromatic hydroxy compound, an alkyl aryl carbonate and a mixture thereof, wherein the starting material and the reactant are continuously fed to a continuous multistage distillation column to effect a transesterification reaction therebetween in the presence of a catalyst in the distillation column, while continuously withdrawing the produced aromatic carbonate or aromatic carbonate mixture as a high boiling point product in a liquid form from a lower portion of the distillation column and continuously withdrawing the by-product as a low boiling point product in a gaseous form from an upper portion of the distillation column by distillation, thereby enabling the aromatic carbonate or aromatic carbonate mixture to be produced continuously. By the method of the present invention, an aromatic carbonate, which is useful as a material for the production of aromatic polycarbonates without using poisonous phosgene or as a material for the production of various isocyanates without using poisonous phosgene, can be produced not only at a high reaction rate but also in a high yield with a high selectivity.

16 Claims, 5 Drawing Sheets

PROCESS FOR CONTINUOUSLY PRODUCING AN AROMATIC CARBONATE

DESCRIPTION

1. Technical Field

The present invention relates to a process for continuously producing an aromatic carbonate. More particularly, the present invention is concerned with a process comprising transesterifying a starting material selected from the group consisting of a dialkyl carbonate represented by

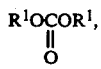

an alkyl aryl carbonate represented by

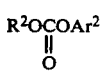

and a mixture thereof with a reactant selected from the group consisting of an aromatic hydroxy compound represented by $Ar^1OH$, an alkyl aryl carbonate represented by

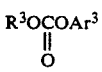

and a mixture thereof, to thereby produce an aromatic carbonate or aromatic carbonate mixture corresponding to the starting material and the reactant and represented by

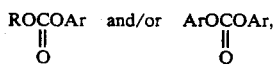

wherein R and Ar are, respectively, selected from $R^1$, $R^2$ and $R^3$ and selected from $Ar^1$, $Ar^2$ and $Ar^3$ in correspondence to the starting material and the reactant, wherein the starting material and the reactant are continuously fed to a continuous multi-stage distillation column to effect a transesterification reaction therebetween in the presence of a catalyst in the distillation column, while continuously withdrawing the aromatic carbonate or aromatic carbonate mixture produced as a high boiling point product in a liquid form from a lower portion of the distillation column and continuously withdrawing a by-product produced as a low boiling point product in a gaseous form from an upper portion of the distillation column by distillation, thereby enabling the aromatic carbonate or aromatic carbonate mixture to be produced continuously with high efficiency.

2. Background Art

An aromatic carbonate is useful as a raw material for the production of an aromatic polycarbonate (whose utility as engineering plastics has been increasing in recent years) without using poisonous phosgene, or as a raw material for the production of various isocyanates without using poisonous phosgene. With respect to the method for the production of an aromatic carbonate, a method for producing an aromatic carbonate or an aromatic carbonate mixture, is known, in which a dialkyl carbonate, an alkyl aryl carbonate or a mixture thereof is used as a starting material and an aromatic hydroxy compound, an alkyl aryl carbonate or a mixture thereof is used as a reactant, and in which a transesterification reaction is performed between the starting material and the reactant.

However, since this type of transesterification is a reversible reaction in which, moreover, not only is the equilibrium biased toward the original system but the reaction rate is also low, the production of an aromatic carbonate by the above-mentioned method on an industrial scale is accompanied with great difficulties.

To improve the above-mentioned method, several proposals have been made, most of which relate to the development of a catalyst for increasing the reaction rate. As a catalyst for use in the method for producing an alkyl aryl carbonate, a diaryl carbonate or a mixture thereof by reacting a dialkyl carbonate with an aromatic hydroxy compound, there have been proposed various catalysts, which include for example, a Lewis acid, such as a transition metal halide, or compounds capable of forming a Lewis acid, [Japanese Patent Application Laid-Open Specification No. 51-105032, Japanese Patent Application Laid-Open Specification No. 56-123948 and Japanese Patent Application Laid-Open Specification No. 56-123949 (corresponding to West German Patent Application Laid-Open Specification No. 2528412, British Patent No. 1499530 and U.S. Pat. No. 4,182,726)], a tin compound, such as an organotin alkoxide and an organotin oxide [Japanese Patent Application Laid-Open Specification No. 54-48733 (corresponding to West German Patent Application Laid-Open Specification No. 2736062), Japanese Patent Application Laid-Open Specification No. 54-63023, Japanese Patent Application Laid-Open Specification No. 60-169444 (corresponding to U.S. Pat. No. 4,554,110), Japanese Patent Application Laid-Open Specification No. 60-169445 (corresponding to U.S. Pat. No. 4,552,704), Japanese Patent Application Laid-Open Specification No. 62-277345, and Japanese Patent Application Laid-Open Specification No. 1-265063], salts and alkoxides of an alkali metal or an alkaline earth metal (Japanese Patent Application Laid-Open Specification No. 56-25138), lead compounds (Japanese Patent Application Laid-Open Specification No. 57-176932), complexes of a metal, such as copper, iron and zirconium (Japanese Patent Application Laid-Open Specification No. 57-183745), titanic acid esters [Japanese Patent Application Laid-Open Specification No. 58-185536 (corresponding to U.S. Pat. No. 4,410,464)], a mixture of a Lewis acid and protonic acid [Japanese Patent Application Laid-Open Specification No. 60-173016 (corresponding to U.S. Pat. No. 4,609,501)], compounds of Sc, Mo, Mn, Bi, Te or the like (Japanese Patent Application Laid-Open Specification No. 1-265064), and ferric acetate (Japanese Patent Application Laid-Open Specification No. 61-172852).

As a catalyst for use in the method for producing a diaryl carbonate by performing disproportionation by means of a same-species intermolecular transesterification of an alkyl aryl carbonate into a diaryl carbonate and a dialkyl carbonate, there have been proposed various catalysts, which include for example, a Lewis acid and a transition metal compound which is capable of forming a Lewis acid [Japanese Patent Application Laid-Open Specification No. 51-75044 (corresponding to West German Patent Application Laid-Open Specification No. 2552907 and U.S. Pat. No. 4,045,464)], a polymeric tin compound [Japanese Patent Application Laid-Open Specification No. 60-169444 (corresponding to U.S. Pat. No. 4,554,110)], a compound represented by the formula R—X(=O)OH (wherein X is selected from Sn and Ti, and R is selected from monovalent hydrocarbon residues) [Japanese Patent Application Laid-Open Specification No. 60-169445 (corresponding to U.S. Pat. No. 4,552,704)], a mixture of a Lewis acid and protonic acid [Japanese Patent Application Laid-Open Specification No. 60-173016 (corresponding to U.S. Pat. No. 4,609,501)], a lead catalyst (Japanese Patent Application Laid-Open Specification No. 1-93560), a titanium or zirconium compound (Japanese Patent Application Laid-Open Specification No. 1-265062), a tin compound (Japanese Patent Application Laid-Open Specification No. 1-265063), and a compound of Sc, Mo, Mn, Bi, Te or the like (Japanese Patent Application Laid-Open Specification No. 1-265064).

However, the effective improvement of reaction rate cannot be attained by the methods using the above-mentioned various catalysts, and therefore, it has been impossible to produce an aromatic carbonate at high selectivity and in high yield by a short-time reaction.

Another attempt for improving the yield of aromatic carbonates in these reactions consists in biasing the equilibrium toward the product system as much as possible. In the case of producing an aromatic carbonate from a dialkyl carbonate and an aromatic hydroxy compound, there have been proposed for example, a method in which by-produced methanol is distilled off together with an azeotrope forming agent by azeotropic distillation in the reaction of a dimethyl carbonate with phenol [Japanese Patent Application Laid-Open Specification No. 54-48732 (corresponding to West German Patent Application Laid-Open Specification No. 2736063) and Japanese Patent Application Laid-Open Specification No. 61-291545] and a method in which by-produced methanol is removed by adsorbing the same onto a molecular sieve [Japanese Patent Application Laid-Open Specification No. 58-185536 (corresponding to U.S. Pat. No. 410,464)].

However, in the method described in Japanese Patent Application Laid-Open Specification No. 54-48732, a complicated step is required to separate and collect a large quantity of heptane used as an azeotrope forming agent from an azeotrope. In addition, in this method as well, the yield of an aromatic carbonate is as small as 3.5% relative to the phenol used even after the reaction for a period as long as 45 hours.

Further, in the method described in Japanese Patent Application Laid-Open Specification No. 58-185536, not only is a large quantity of molecular sieve as much as 8-10 g per g of the methanol by-produced necessary, but also a complicated step is required for desorbing the methanol adsorbed on the molecular sieve.

Therefore, it is difficult to carry out these methods on a commercial scale.

Furthermore, as a method for performing the intended reaction, which is preferred among the methods of the above-described proposals, it is known to employ an apparatus comprising a reactor provided on the top thereof with columns having distillation function or fractional distillation function in order to separate and distill off alcohols (by-produced in the course of the reaction) from a mixture of the starting material, the product and the solvent co-present therewith [Japanese Patent Application Laid-Open Specification No. 56-123948 (corresponding to U.S. Pat. No. 4,182,726), Japanese Patent Application Laid-Open Specification No. 56-25138, Japanese Patent Application Laid-Open Specification No. 60-169444 (corresponding to U.S. Pat. No. 4,554,110), Japanese Patent Application Laid-Open Specification No. 60-169445 (corresponding to U.S. Pat. No. 4,552,704), Japanese Patent Application Laid-Open Specification No. 60-173016 (corresponding to U.S. Pat. No. 4,609,501), Japanese Patent Application Laid-Open Specification No. 61-172852, Japanese Patent Application Laid-Open Specification No. 61-291545, and Japanese Patent Application Laid-Open Specification No. 62-277345].

However, in all of the above-mentioned methods, the reaction proceeds only in the reactor in which a catalyst is present. The distillation column provided at the top of the reactor is used only to separate the alcohols (produced in the reactor) from the other components present in the reactor. This is apparent from the detailed description of Japanese Patent Application Laid-Open Specification No. 61-291545. In the Laid-Open specification, for example, there is a description "in such a reaction, generally, a reaction distillation method is employed, in which using a reaction-distillation apparatus in which a reactor is provided with a distillation column, methanol having a boiling point lower than that of the desired carbonate as formed is distilled off from the top of the column while performing the desired reaction in the reactor disposed at the bottom of the column" (page 1, right hand column, lines 12-17 of the Laid-Open specification).

That is, the reaction distillation method in these conventional methods is performed by the use of an apparatus in which a reacting part and a distilling part separately exist. In the part of the distillation column, only distillation is performed but no reaction is conducted. Thus, in these conventional methods, a reaction is performed in a liquid phase in the reactor, but the equilibrium of the reaction is biased toward the product system only by the withdrawal of the low boiling point alcohols by-produced from the liquid phase to a gas phase through a gas-liquid interface to thereby proceed the reaction However, the reactor used in these methods is of a vessel type, so that the gas-liquid interfacial area is as small as being approximately equal to the cross section area of the reactor, inevitably causing the reaction to be extremely slow, as known in the art. For example, in working examples of Japanese Patent Application Laid-Open Specification Nos. 61-291545, 54-48732 and 54-48733, it takes a reaction time as long as 8-45 hours for a batch system. In the method in which such a prolonged period of time is taken, not only the side-reactions of a starting material or an intermediate product but also the side-reactions of the aromatic carbonates produced are likely to occur to thereby cause a lowering in selectivity. Furthermore, in these reaction methods which take such a prolonged period of time, the productivity is poor, and hence, it is difficult to perform these methods on a commercial scale.

Moreover, with respect to the method known as reaction distillation using an apparatus in which a reacting part and a distilling part are separately disposed, Japanese Patent Application Laid-Open Specification No 61-291545 has a description to the following effect although the reaction distillation operation can be conducted in a batch-wise manner or in a continuous manner, the batch-wise operation is preferred for example, when a dimethyl carbonate is subjected to transesterification with phenol, since the continuous operation requires large-size facilities due to a low reaction rate" (page 3, left hand lower column, lines 4-9). In fact, in all of the working examples of the various publications described above, there is employed either a method in which both of a dialkyl carbonate and an aromatic hydroxy compound as reaction agents are charged together with a catalyst into a reactor from the beginning to effect a reaction, or a method in which only one of the reaction agents (generally, an aromatic hydroxy compound which is a high boiling point compound) is first charged together with a catalyst into a reactor, followed by a reaction while feeding the other reaction agent. Both of the methods are of a batch system Therefore, up to now, there has been no publication disclosing a continuous reaction method in which both reaction agents are continuously fed while continuously withdrawing products.

DISCLOSURE OF THE INVENTION

In the above-described situation, the present inventors have made extensive and intensive studies to develop a process free of the drawbacks of the various hitherto proposed processes as mentioned above, which process realizes the continuous production of an aromatic carbonate at a high reaction rate and with a high selectivity. As a result, it has surprisingly been found that an aromatic carbonate or an aromatic carbonate mixture can be continuously produced efficiently at a high reaction rate and with a high selectivity by continuously feeding a starting material and a reactant to a continuous multi-stage distillation column to effect a transesterification reaction therebetween in the presence of a catalyst in the distillation column, while continuously withdrawing the produced aromatic carbonate or aromatic carbonate mixture as a high boiling point product in a liquid form from a lower portion of the distillation column and continuously withdrawing the by-product as a low boiling point product in a gaseous form from an upper portion of the distillation column by distillation. Further, it has been found that the desired aromatic carbonate or aromatic carbonate mixture can be continuously produced more efficiently by employing a plurality of continuous multi-stage distillation columns in combination so as to effect a skillful recycling of high boiling point products and/or low boiling point products.

The present invention has been made on the basis of these findings.

Accordingly, it is an object of the present invention to provide a novel process for continuously producing an aromatic carbonate efficiently at a high reaction rate and with a high selectivity by using a continuous multi-stage distillation column as a reaction column.

It is another object of the present invention to provide a process in which the desired aromatic carbonate is produced more efficiently by the use of a plurality of continuous multi-stage distillation columns.

Figure 1:
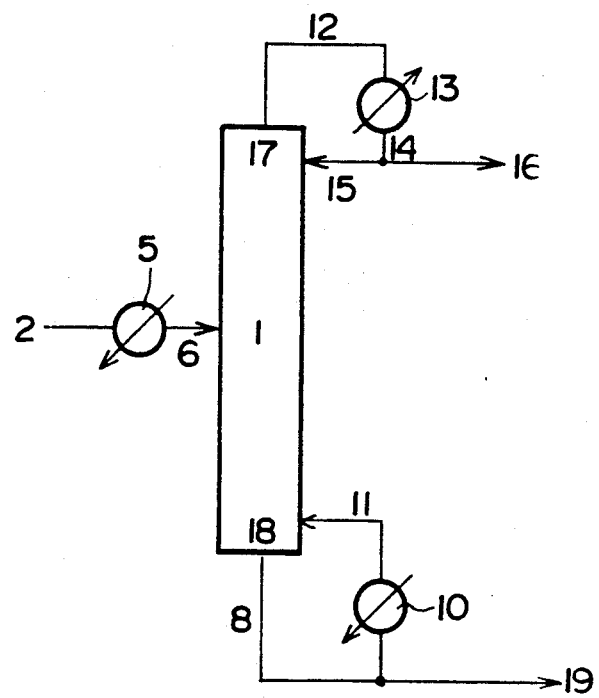
FIG. 1, FIG. 2, FIG. 3, FIG. 4 and FIG. 5 are diagrams showing various modes of processes for practicing the process of the present invention.

Essentially, according to the present invention, there is provided a process for producing an aromatic carbonate which comprises transesterifying a starting material selected from the group consisting of a dialkyl carbonate represented by

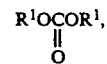

an alkyl aryl carbonate represented by

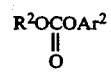

and a mixture thereof with a reactant selected from the group consisting of an aromatic hydroxy compound represented by Ar$^1$OH, an alkyl aryl carbonate represented by

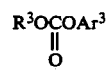

and a mixture thereof, wherein each of R$^1$, R$^2$ and R$^3$ independently represents an alkyl group having 1 to 10 carbon atoms, an alicyclic group having 3 to 10 carbon atoms or an aralkyl group having 6 to 10 carbon atoms and each of Ar$^1$, Ar$^2$ and Ar$^3$ independently represents an aromatic group having 5 to 30 carbon atoms, to thereby produce an aromatic carbonate or aromatic carbonate mixture corresponding to the starting material and the reactant and represented by

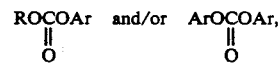

wherein R and Ar are, respectively, selected from R$^1$, R$^2$ and R$^3$ and selected from Ar$^1$, Ar$^2$ and Ar$^3$ in correspondence to the starting material and the reactant and produce an aliphatic alcohol, a dialkyl carbonate or a mixture thereof corresponding to the starting material and the reactant and represented by ROH and/or

wherein R is as defined above, as a by-product, characterized in that the starting material and the reactant are continuously fed to a continuous multi-stage distillation column to effect a liquid phase and/or gas-liquid phase transesterification reaction therebetween in the presence of a catalyst in the distillation column, while continuously withdrawing a high boiling point reaction mixture containing the produced aromatic carbonate or aromatic carbonate mixture in a liquid form from a lower portion of the distillation column and continuously withdrawing a low boiling point reaction mixture containing the by-product in a gaseous form from an upper portion of the distillation column by distillation, thereby enabling the aromatic carbonate or aromatic carbonate mixture to be produced continuously.

The typical reactions which are involved in the process of the present invention are represented by the following formulae:

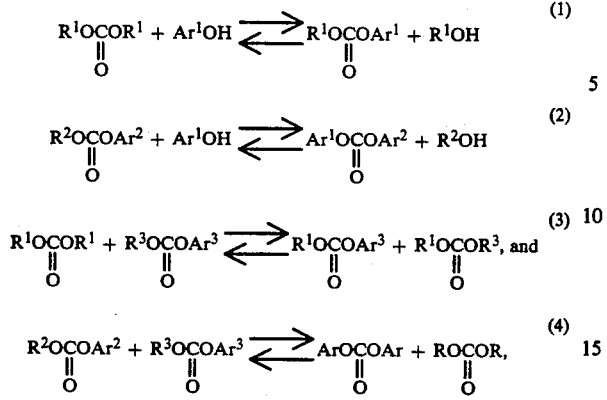

(1) $R^1OCOR^1 + Ar^1OH \rightleftharpoons R^1OCOAr^1 + R^1OH$ (2) $R^2OCOAr^2 + Ar^1OH \rightleftharpoons Ar^1OCOAr^2 + R^2OH$ (3) $R^1OCOR^1 + R^3OCOAr^3 \rightleftharpoons R^1OCOAr^3 + R^1OCOR^3$, and (4) $R^2OCOAr^2 + R^3OCOAr^3 \rightleftharpoons ArOCOAr + ROCOR$, wherein $R^1$, $R^2$, $R^3$, $Ar^1$, $Ar^2$ and $Ar^3$ are as defined above, each of Ar's appearing in formula (4) independently represents $Ar^2$ or $Ar^3$, and each of R's appearing in formula (4) independently represents $R^2$ or $R^3$, and wherein when $R^2 = R^3$ and $Ar^2 = Ar^3$ in formula (4), the reaction is a same species-intermolecular transesterification reaction generally known as a disproportionation reaction.

The essential feature of the process of the present invention resides in that the above reactions are performed in the presence of a catalyst in a continuous multi-stage distillation column while separating the low boiling point products formed by the reactions from the reaction system by distillation. The continuous production of an aromatic carbonate at a high selectivity and in a high yield has for the first time become feasible by virtue of this process.

It is really an unexpected finding that the reaction according to the present invention, the equilibrium of which is extremely biased toward the original system [for example, the equilibrium constant of the reaction defined by formula (1) is in the order of $10^{-3}$ to $10^{-4}$], can be advanced at a high reaction rate by the above process to thereby enable an aromatic carbonate to be continuously produced at a high selectivity and in a high yield.

It is surprising that in the process of the present invention the reaction rate is high and the selectivity and yield (or productivity) are markedly improved as compared to those attained by the conventional processes. The exact reason has not yet been elucidated. However, in light of the results of the practice of the process of the present invention, the following presumptions can be made.

That is, all of the reactions of the above formulae (1) to (4), which are involved in the process of the present invention, are reversible reactions, in which the equilibrium is extremely biased toward the original system. Therefore, in all of the reactions, in order to increase the conversion ratio, it is necessary to remove a by-product, which is comprised of low boiling point products formed in the reaction [generally, aliphatic alcohols in the reactions of formulae (1) and (2) and dialkyl carbonates in the reactions of formulae (3) and (4)], from the liquid phase in the reaction system as promptly as possible.

However, it has not been possible to increase a reaction rate in the conventional process in which the reaction is conducted using a tank reactor provided in an upper portion thereof with a distillation column as described in the above-mentioned various publications showing the prior art. The reason is that not only is the reaction site limited to only the tank reactor portion where a catalyst is present but the area of a gas-liquid interface necessary for evaporating the low boiling point products formed by the reaction from the liquid phase in the reactor into a gas phase is also small.

By contrast, in the process of the present invention, a catalyst is present throughout a continuous multi-stage distillation column and, hence, it is possible to advance the reaction in a large region in which an area of a gas-liquid interface is extremely large. In this region, a fed liquid material to be reacted flows down while repeatedly experiencing gas-liquid contact with a vapor ascending from a lower portion and experiencing distillation and reaction. At that time, the low boiling point products are evaporated from the liquid phase into a vapor phase. As a result, each component within the continuous multi-stage distillation column comes to have a biased concentration distribution. For example, when the reactions of formulae (1) and (2) are performed, generally, the concentration of an alkyl aryl carbonate and/or a diaryl carbonate as a high boiling point product in the liquid phase has a distribution such that the concentration gradually increases from the highest stage of the stages in which a catalyst is present toward the lower portion of the column. On the other hand, the concentration of an aliphatic alcohol as a low boiling point product in the liquid phase usually has a distribution such that the concentration gradually decreases from the top portion of the column toward the lower portion of the column. Around the lowermost portion of the column, it is possible to reduce the aliphatic alcohol concentration in the liquid phase to an extremely low level. In the vapor phase, the aliphatic alcohol concentration has a distribution such that it gradually increases from the lower portion of the column toward the upper portion of the column.

When for example, the reactions of formulae (3) and (4) are performed, the concentration of a diaryl carbonate as a high boiling point product in the liquid phase generally has a distribution such that the concentration gradually increases from the highest one of the stages of the column in which a catalyst is present toward the lower portion of the column. On the other hand, the concentration of a dialkyl carbonate as a low boiling point product in the liquid phase usually has a distribution such that the concentration gradually decreases from the upper portion of the column toward the lower portion of the column. Around the lowermost portion of the column, it is possible to reduce the dialkyl carbonate concentration in the liquid phase to an extremely low level. In the vapor phase, the dialkyl carbonate concentration has a distribution such that it gradually increases from the lowermost portion of the column toward the upper portion of the column.

In the process of the present invention, the above reactions proceed as described above in a continuous multi-stage distillation column. It is believed that at an arbitrary position within such a reaction region, the liquid phase of the reaction system is in a condition close to an equilibrium composition as a result of the reaction and the vapor phase has a composition close to a gas-liquid equilibrium condition relative to the liquid phase. Accordingly, when the liquid phase is retained at that position, the reaction is no longer advanced. However, actually, it is possible to further advance the reaction by allowing the liquid phase to flow down so as to effect a gas-liquid contact with a vapor phase in which the concentration of a low boiling point reaction product is lower, thereby further increasing the concentration of an aromatic carbonate as a high boiling point product in the liquid phase.

In the conventional process in which a reaction is performed in a tank reactor provided in the upper portion thereof with a distillation column, a reaction is performed only in the tank reactor, and the distillation column functions only for separating from the low boiling point starting compound vapor a low boiling point product vapor coming from a gas-liquid interface into a gas phase in the tank reactor and allowing the low boiling point starting compound in a liquid form to flow down back to the tank reactor.

Therefore, it is believed that the advantages of the process of the present invention over the conventional process are mainly due to the following points:

(1) the area of a gas-liquid interface can be extremely large as compared to that provided by the conventional process in which the reaction is performed using a tank reactor, and as a result, the mass transfer of a low boiling point product as a by-product to the vapor phase is facilitated;

(2) the liquid phase of the reaction system in a continuous multi-stage distillation column flows down while repeatedly experiencing a gas-liquid contact with a vapor ascending from a lower portion and being subjected to reaction and, hence, despite the fact that the process of the present invention is a continuous process, high conversions of the starting material and the reactant can be achieved (in the conventional process in which the reaction is conducted using a tank reactor, it is difficult to increase the conversion of the starting compound even if the desired aromatic carbonate is continuously withdrawn, and no continuous process has actually been proposed. For increasing the conversion in the conventional process, it is necessary to conduct the reaction in a batchwise manner for a prolonged period of time); and (3) the vapor ascending in a continuous multi-stage distillation column ascends while repeatedly experiencing a gas-liquid contact with a liquid descending in the column and, hence, the thermal energy of the vapor is effectively utilized.

The dialkyl carbonate to be used as a starting material in the present invention is represented by formula

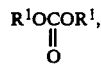

wherein $R^1$ represents an alkyl group having 1 to 10 carbon atoms, an alicyclic group having 3 to 10 carbon atoms or an aralkyl group having 6 to 10 carbon atoms. Examples of $R^1$ include an alkyl group, such as methyl, ethyl, propyl (isomers), allyl, butyl (isomers), butenyl (isomers), pentyl (isomers), hexyl (isomers), heptyl (isomers), octyl (isomers), nonyl (isomers), decyl (isomers) and cyclohexylmethyl; an alicyclic group, such as cyclopropyl, cyclobutyl, cyclopentyl, cyclohexyl and cycloheptyl; and an aralkyl group, such as benzyl, phenethyl (isomers), phenylpropyl (isomers), phenylbutyl (isomers) and methylbenzyl (isomers).

The above-mentioned alkyl group, alicyclic group and aralkyl group may be substituted with a substituent, such as a lower alkyl group, a lower alkoxy group, a cyano group and a halogen atom, as long as the number of carbon atoms of the substituted group does not exceed 10, and may also contain an unsaturated bond.

As a dialkyl carbonate having such $R^1$, there may be mentioned for example, dimethyl carbonate, diethyl carbonate, dipropyl carbonate (isomers), diallyl carbonate, dibutenyl carbonate (isomers), dibutyl carbonate (isomers), dipentyl carbonate (isomers), dihexyl carbonate (isomers), diheptyl carbonate (isomers), dioctyl carbonate (isomers), dinonyl carbonate (isomers), didecyl carbonate (isomers), dicyclopentyl carbonate, dicyclohexyl carbonate, dicycloheptyl carbonate, dibenzyl carbonate, diphenyl carbonate (isomers), di(phenylpropyl) carbonate (isomers), di(phenylbutyl) carbonate (isomers), di(chlorobenzyl) carbonate (isomers), di(methoxybenzyl) carbonate (isomers), di(methoxymethyl) carbonate, di(methoxyethyl) carbonate (isomers), di(chloroethyl) carbonate (isomers) and di(cyanoethyl) carbonate (isomers).

Of these dialkyl carbonates, a dialkyl carbonate containing as $R^1$ a lower alkyl group having 4 or less carbon atoms is preferably used. Most preferred is dimethyl carbonate.

The aromatic hydroxy compound to be used as a reactant in the present invention is represented by formula $Ar^1OH$ wherein $Ar^1$ represents an aromatic group having 5 to 30 carbon atoms, and the type of the compound is not limited as long as the hydroxyl group is directly bonded to the aromatic group. Examples of $Ar^1$ include a phenyl group and various alkylphenyl groups, such as phenyl, tolyl (isomers), xylyl (isomers), trimethylphenyl (isomers), tetramethylphenyl (isomers), ethylphenyl (isomers), propylphenyl (isomers), butylphenyl (isomers), diethylphenyl (isomers), methylethylphenyl (isomers,), pentylphenyl (isomers), hexylphenyl (isomers) and cyclohexylphenyl (isomers); various alkoxyphenyl groups, such as methoxyphenyl (isomers), ethoxyphenyl (isomers) and butoxyphenyl (isomers); various halogenated phenyl groups, such as fluorophenyl (isomers), chlorophenyl (isomers), bromophenyl (isomers), chloromethylphenyl (isomers) and dichlorophenyl (isomers); various substituted phenyl groups represented by the formula:

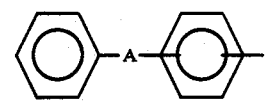

wherein A represents a bond, a divalent group, such as —O—, —S—, —CO— and —SO$_2$—, an alkylene group, a substituted alkylene group of the formula:

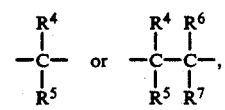

wherein each of $R^4$, $R^5$, $R^6$ and $R^7$ individually represents a hydrogen atom, a lower alkyl group, a cycloalkyl group, an aryl group or an aralkyl group, which may be substituted with a halogen atom or an alkoxy group),
or a cycloalkylene group of the formula:

wherein k is an integer of from 3 to 11, and the hydrogen atoms may be substituted with a lower alkyl group, an aryl group, a halogen atom or the like, and
the aromatic group may be substituted with a substituent, such as a lower alkyl group, a lower alkoxy group, an ester group, a hydroxyl group, a nitro group, a halogen and a cyano group;
a naphthyl group and various substituted naphthyl groups, such as naphthyl (isomers), methylnaphthyl (isomers), dimethylnaphthyl (isomers), chloronaphthyl (isomers), methoxynaphthyl (isomers) and cyanonaphthyl (isomers); and various unsubstituted or substituted heteroaromatic groups, such as pyridyl (isomers), cumaryl (isomers), quinolyl (isomers), methylpyridyl (isomers), chloropyridyl (isomers), methylcumaryl (isomers) and methylquinolyl (isomers).

Examples of aromatic hydroxy compounds having these $Ar^1$ include phenol; various alkyl phenols, such as cresol (isomers), xylenol (isomers), trimethylphenol (isomers), tetramethylphenol (isomers), ethylphenol (isomers), propylphenol (isomers), butylphenol (isomers), diethylphenol (isomers), methylethylphenol (isomers), methylpropylphenol (isomers), dipropylphenol (isomers), methylbutylphenol (isomers), pentylphenol (isomers), hexylphenol (isomers) and cyclohexylphenol (isomers); various alkoxyphenols, such as methoxyphenol (isomers) and ethoxyphenol (isomers); various substituted phenols represented by the formula:

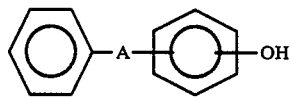

wherein A is as defined above; naphthol (isomers) and various substituted naphthols; and heteroaromatic hydroxy compounds, such as hydroxypyridine (isomers), hydroxycumarine (isomers) and hydroxyquinoline (isomers). Also usable are an aromatic dihydroxy compound having two hydroxyl groups, such as hydroquinone, resorcinol, catechol, dihydroxynaphthalene, dihydroxyanthracene and a dihydroxy compound obtained by substitution of the above with an alkyl group; and an aromatic dihydroxy compound represented by the formula:

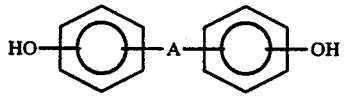

A is as defined above, and the aromatic ring may be substituted with a substituent, such as a lower alkyl group, a lower alkoxy group, an ester group, a nitro group, a cyano group and a halogen atom.

Of these aromatic hydroxy compounds, an aromatic monohydroxy compound containing as $Ar^1$ an aromatic group having 6 to 10 carbon atoms is preferably used in the present invention, and phenol is most preferred.

The alkyl aryl carbonate to be used as a starting material in the present invention is represented by the formula:

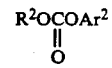

wherein $R^2$ may be identical with or different from $R^1$, and represents an alkyl group having 1 to 10 carbon atoms, an alicyclic group having 3 to 10 carbon atoms or an aralkyl group having 6 to 10 carbon atoms; and $Ar^2$ may be identical with or different from $Ar^1$, and represents an aromatic group having 5 to 30 carbon atoms. As $R^2$, there may be mentioned for example, the same groups as set forth above for $R^1$. As $Ar^2$, there may be mentioned for example, the same groups as set forth above for $Ar^1$.

Representative examples of alkyl aryl carbonate having these $R^2$ and $Ar^2$ include methyl phenyl carbonate, ethyl phenyl carbonate, propyl phenyl carbonate (isomers), allyl phenyl carbonate, butyl phenyl carbonate (isomers), pentyl phenyl carbonate (isomers), hexyl phenyl carbonate (isomers), heptyl phenyl carbonate (isomers), octyl tolyl carbonate (isomers), nonyl ethylphenyl carbonate (isomers), decyl butylphenyl carbonate (isomers), methyl tolyl carbonate (isomers), ethyl tolyl carbonate (isomers), propyl tolyl carbonate (isomers), butyl tolyl carbonate (isomers), allyl tolyl carbonate (isomers), methyl xylyl carbonate (isomers), methyl trimethylphenyl carbonate (isomers), methyl chlorophenyl carbonate (isomers), methyl nitrophenyl carbonate (isomers), methyl methoxyphenyl carbonate (isomers), methyl cumyl carbonate (isomers), methyl naphthyl carbonate (isomers), methyl pyridyl carbonate (isomers), ethyl cumyl carbonate (isomers), methyl benzoylphenyl carbonate (isomers), ethyl xylyl carbonate (isomers), benzyl xylyl carbonate (isomers), methyl hydroxyphenyl carbonate (isomers), ethyl hydroxyphenyl carbonate (isomers), methoxycarbonyloxybiphenyl (isomers), methyl hydroxybiphenyl carbonate (isomers), methyl 2-(hydroxyphenyl)propylphenyl carbonate (isomers) and ethyl 2-(hydroxyphenyl)-propylphenyl carbonate (isomers). Of these alkyl aryl carbonates, one containing as $R^2$ an alkyl group having 1 to 4 carbon atoms and as $Ar^2$ an aromatic group having 6 to 10 carbon atoms is preferably used, and methyl phenyl carbonate is most preferred.

The alkyl aryl carbonate to be used as a reactant in the present invention is represented by the formula:

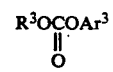

wherein $R^3$ may be identical with or different from $R^1$ and $R^2$, and represents an alkyl groups having 1 to 10 carbon atoms, as alicyclic group having 3 to 10 carbon atoms or an aralkyl group having 6 to 10 carbon atoms; and $Ar^3$ may be identical with or different from $Ar^1$ and $Ar^2$, and represents and aromatic group having 5 to 30 carbon atoms. As $R^3$, there may be mentioned for example, the same groups as set forth above for $R^1$. As $Ar^3$, there may be mentioned for example, the same groups as set forth above for $Ar^1$.

As alkyl aryl carbonates having these $R^3$ and $Ar^3$, there may be mentioned for example, those which are set forth above for

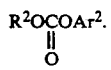

Of these alkyl aryl carbonates, one containing as $R^3$ an alkyl group having 1 to 4 carbon atoms and as $Ar^3$ an aromatic group having 6 to 10 carbon atoms, and methyl phenyl carbonate is most preferred.

When each of the reactions of formulae (1), (2), (3) and (4) is performed according to the process of the present invention, dialkyl carbonates or alkyl aryl carbonates as starting materials for the reaction can be used individually or in mixture and aromatic hydroxy compounds or alkyl aryl carbonates as reactants for the reaction can be used individually or in mixture.

When $R^2=R^3=R$ and $Ar^2=Ar^3=Ar$ in the transesterification reaction of formula (4), a diaryl carbonate and a dialkyl carbonate can be obtained by a same species-intermolecular transesterification reaction of a single type of alkyl aryl carbonate. This is a preferred embodiment of the present invention.

Further, when $R^1=R^2=R^3=R$ and $Ar^1=Ar^2=Ar^3=Ar$ in formulae (1) and (4), by combining the reaction of formula (1) with the reaction of formula (4), a diaryl carbonate can be obtained from a dialkyl carbonate and an aromatic hydroxy compound through an alkyl aryl carbonate as shown in formulae (5) and (6). This is an especially preferred embodiment of the present invention.

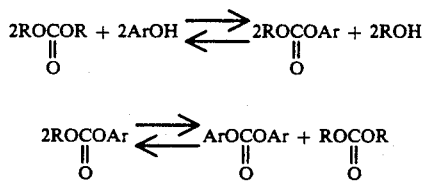

Recycling of the dialkyl carbonate by-produced in the reaction of formula (6) as a starting material for the reaction of formula (5) results in the formation of 1 mol. of a diaryl carbonate and 2 mol. of an aliphatic alcohol from 1 mol. of a dialkyl carbonate and 2 mol. of an aromatic hydroxy compound.

When $R=CH_3$ and $Ar=C_6H_5$ in the above formulae (5) and (6), diphenyl carbonate, which is an important raw material for polycarbonate and an isocyanate, can be readily obtained from dimethyl carbonate, which is the simplest form of dialkyl carbonate, and phenol. This is especially important.

As a catalyst to be used in the present invention, there may be mentioned for example:

Lead Compounds a lead oxides, such as PbO, $PbO_2$ and $Pb_3O_4$; lead sulfides, such as PbS and $Pb_2S$; lead hydroxides, such as $Pb(OH)_2$ and $Pb_2O_2(OH)_2$; plumbites, such as $Na_2PbO_2$, $K_2PbO_2$, $NaHPbO_2$ and $KHPbO_2$; a plumbate, such as $Na_2PbO_3$, $Na_2H_2PbO_4$, $K_2PbO_3$, $K_2[Pb(OH)_6]$, $K_4PbO_4$, $Ca_2PbO_4$ and $CaPbO_3$; lead carbonates and basic salts thereof, such as $PbCO_3$ and $2PbCO_3 \cdot Pb(OH)_2$; lead salts of organic acids, and basic salts thereof, such as $Pb(OCOCH_3)_2$, $Pb(OCOCH_3)_4$ and $Pb(OCOCH_3)_2 \cdot PbO \cdot 3H_2O$; organolead compounds, such as $Bu_4Pb$, $Ph_4Pb$, $Bu_3PbCl$, $Ph_3PbBr$, $Ph_3Pb$ (or $Ph_6Pb_2$), $Bu_3PbOH$ and $Ph_3PbO$ wherein Bu represents a butyl group and Ph represents a phenyl group; alkoxy-lead compounds and aryloxylead compounds, such as $Pb(OCH_3)_2$, $(CH_3O)Pb(OPh)$ and $Pb(OPh)_2$; lead alloys, such as Pb-Na, Pb-Ca, Pb-Ba, Pb-Sn and Pb-Sb; lead minerals, such as galena and zincblende; and hydrates of these lead compounds;

Copper Family Metal Compounds salts or complexes of a copper family metal, such as CuCl, $CuCl_2$, CuBr, $CuBr_2$, CuI, $CuI_2$, $Cu(OAc)_2$, $Cu(acac)_2$, copper oleate, $Bu_2Cu$, $(CH_3O)_2Cu$, $AgNO_3$, AgBr, silver picrate, $AgC_6H_6ClO_4$, $Ag(bullvalene)_3 \cdot NO_3$, $[AuC\equiv C-C(CH_3)_3]_n$ and $[Cu(C_7H_8)Cl]_4$ wherein OAc represents an acetyl group and acac represents an acetylacetone chelate ligand;

Alkali Metal Complexes alkali metal complexes, such as Li(acac) and $LiN(C_4H_9)_2$ wherein acac is as defined above;

Zinc Complexes zinc complexes, such as $Zn(acac)_2$ wherein acac is as defined above;

Cadmium Complexes cadmium complexes, such as $Cd(acac)_2$ wherein acac is as defined above;

Iron Family Metal Compounds $Fe(C_{10}H_8)(CO)_5$, $Fe(CO)_5$, $Fe(C_3H_6)(CO)_3$, $Co(mesitylene)_2(PEt_2Ph)_2$, $CoC_5F_5(CO)_2$, $Ni-n-C_5H_5NO$ and ferrocene;

Zirconium Complexes zirconium complexes, such as $Zr(acac)_4$ wherein acac is as defined above and zirconocene;

Lewis Acids and Lewis Acid-forming Compounds

Lewis acids and Lewis acid-forming transition metal compounds, such as $AlX_3$, $TiX_3$, $TiX_4$, $VOX_3$, $VX_5$, $ZnX_2$, $FeX_3$ and $SnX_4$ wherein X represents a halogen, an acetoxy group, an alkoxy group or an aryloxy group;

Organotin Compounds organotin compounds, such as $(CH_3)_3SnOCOCH_3$, $(C_2H_5)_3SnOCOC_6H_5$, $Bu_3SnOCOCH_3$, $Ph_3SnOCOCH_3$, $Bu_2Sn(OCOCH_3)_2$, $Bu_2Sn(OCOC_{11}H_{23})_2$, $Ph_3SnOCH_3$, $(C_2H_5)_3SnOPh$, $Bu_2Sn(OCH_3)_2$, $Bu_2Sn(OC_2H_5)_2$, $Bu_2Sn(OPh)_2$, $Ph_2Sn(OCH_3)_2$, $(C_2H_5)_3SnOH$, $Ph_3SnOH$, $Bu_2SnO$, $(C_8H_{17})_2SnO$, $Bu_2SnCl_2$ and $BuSnO(OH)$;

Inorganic Oxides inorganic oxides, such as silica, alumina, titania, silicatitania, zinc oxide, zirconium oxide, gallium oxide, zeolite and an oxide of a rare earth; and a material obtained by modifying the surface acid site of the above inorganic oxide by silylation or other methods.

These catalysts may be either soluble or insoluble in the liquid phase of the reaction system. Further, these catalysts may be used in the form of a mixture with a compound or a carrier which is inert to the reaction or a composite having the catalyst supported on such a compound or a carrier.

These catalysts are effective even when they are reacted with an organic compound present in the reaction system, such as an aliphatic alcohol, an aromatic hydroxy compound, an alkyl aryl carbonate, a diaryl carbonate and a dialkyl carbonate. Alternatively, these catalysts may be heat treated with a feedstock, i.e., a starting material and a reactant, or a corresponding product prior to the use in the process of the present invention.

Of these catalysts, especially preferred are lead compounds, for example, lead oxides, such as PbO, $PbO_2$ and $Pb_3O_4$, lead hydroxides, such as $Pb(OH)_2$ and $Pb_2O_2(OH)_2$, lead carbonates and basic salts thereof, such as $PbCO_3$ and $2PbCO_3.Pb(OH)_2$, alkoxylead compounds and aryloxylead compounds, such as $Pb(OCH_3)_2$, $(CH_3O)Pb(OPh)$ and $Pb(OPh)_2$. Further, those which are formed by reacting such a lead compound with an organic compound present in the reaction system and those which are obtained by heat treating, prior to the reaction, such a lead compound with a feedstock, i.e., a starting material and a reactant, or a corresponding product, may preferably be used.

There is no limitation with respect to the continuous multi-stage distillation column to be used in the present invention as long as it is a distillation column having a theoretical number of plates of distillation of two or more and which is capable of continuous distillation. Examples of such continuous multistage distillation columns include plate type columns using a tray, such as a bubble-cap tray, a sieve tray, a valve tray and a counterflow tray, and packed type columns packed with various packings, such as a Raschig ring, a Lessing ring, a Pall ring, a Berl saddle, an Intelox saddle, a Dixon packing, a McMahon packing, a Heli pack, a Sulzer packing and Mellapak. Any column which is generally used as a continuous multi-stage distillation column can be utilized. (In the present invention, "the number of stages of a distillation column" means the number of plates with respect to a plate column and the number of theoretical plates with respect to the other types of distillation columns including a packed column.) Further, a mixed type of plate column and packed column comprising both a plate portion and a portion packed with packings, can also be preferably used. When a solid catalyst which is insoluble in the liquid phase in a distillation column is used, a packed column type distillation column in which the solid catalyst is used in substitution for part or all of the packings, is preferably employed.

In the present invention, it is requisite that a catalyst be present in the continuous multi-stage distillation column, and it is preferred that the catalyst be present in at least two plates of the continuous multi-stage distillation column.

The method for allowing a catalyst to be present in the continuous multi-stage distillation column is not limited For example, when a homogeneous catalyst soluble in the liquid phase in the distillation column is used, the catalyst can be allowed to be present in the reaction system by continuously feeding the catalyst to the distillation column, and when a heterogeneous catalyst (solid catalyst) insoluble in the liquid phase in the distillation column is used, the catalyst can be allowed to be present in the reaction system by disposing the solid catalyst in the distillation column. These methods can be used in combination.

When a homogeneous catalyst is continuously fed to the distillation column, it may be fed to the column simultaneously with the feedstock in the form of a mixture of the catalyst and either one or both of the starting material and the reactant. Alternatively, the homogeneous catalyst may be fed to a plate which is different from the plate where the feedstock is fed. Further, the catalyst can be fed at any position as long as the position is at least one plate above the column bottom. However, since the region where the reaction actually takes place in the distillation column is generally below the position where the catalyst is fed, it is preferred that the catalyst be fed to a region between the column top and the position for feeding the feedstock. When a heterogeneous solid catalyst is used, the catalyst can be packed in a desired quantity in a desired position of the distillation column, as long as the theoretical number of stages for the layer in which the catalyst is present is at least one, preferably at least two. This solid catalyst also serves as a packing for the distillation column.

In a region of the column where no catalyst is present, the distillation column serves only as an ordinary distillation column, for example, functions for concentration of the reaction product.

As described above, the process according to the essential aspect of the present invention is a process for producing an aromatic carbonate which comprises transesterifying a starting material selected from the group consisting of a dialkyl carbonate represented by

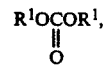

an alkyl aryl carbonate represented by

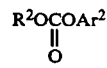

and a mixture thereof with a reactant selected from the group consisting of an aromatic hydroxy compound represented by $Ar^1OH$, an alkyl aryl carbonate represented by

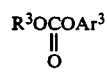

and a mixture thereof, wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms and each of $Ar^1$, $Ar^2$ and $Ar^3$ independently represents an aromatic group having 5 to 30 carbon atoms, to thereby produce an aromatic carbonate or aromatic carbonate mixture corresponding to the starting material and the reactant and represented by

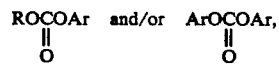

wherein R and Ar are, respectively, selected from $R^1$, $R^2$ and $R^3$ and selected from $Ar^1$, $Ar^2$ and $Ar^3$ in correspondence to the starting material and the reactant and produce an aliphatic alcohol, a dialkyl carbonate or a mixture thereof corresponding to the starting material and the reactant and represented by ROH and/or

wherein R is as defined above, as a by-product, characterized in that the starting material and the reactant are continuously fed to a continuous multi-stage distillation column to effect a liquid phase and/or gas-liquid phase transesterification reaction therebetween in the presence of a catalyst in the distillation column, while continuously withdrawing a high boiling point reaction mixture containing the produced aromatic carbonate or aromatic carbonate mixture in a liquid form from a lower portion of the distillation column and continuously withdrawing a low boiling point reaction mixture containing the by-product in a gaseous form from an upper portion of the distillation column by distillation, thereby enabling the aromatic carbonate or aromatic carbonate mixture to be produced continuously. There is no particular restriction with respect to the method for continuously feeding the starting material and the reactant to the continuous multi-stage distillation column, and any feeding method can be used as long as the starting material and the reactant can be contacted with the catalyst in a region of the distillation column which corresponds to at least one plate, preferably at least two plates. For example, the starting material and the reactant can be continuously fed to the continuous multi-stage distillation column from a desired number of feeding pipes onto a desired plate. The starting material and the reactant may be fed either to the same plate of the distillation column or individually to separate plates.

The starting material and the reactant are continuously fed in a liquid form, a gaseous form, or a liquid-gas form.

Besides the feeding of the starting material and the reactant to the continuous multi-stage distillation column as described above, it is also preferred to additionally feed the starting material and/or the reactant in a gaseous form to the lower portion of the distillation column intermittently or continuously.

Also preferable is a method wherein the higher boiling point component of the feedstock composed of the starting material and the reactant is continuously fed in a liquid form or a liquid-gas mixture form to a plate at a level higher than the plate where the catalyst is present, while the lower boiling point component of the feedstock is continuously fed in a gaseous form to the lower portion of the distillation column. In this case, some of the lower boiling point component of the feedstock may be contained in the higher boiling point component of the feedstock fed to the upper portion of the column.

The feedstock may contain products, i.e., an aliphatic alcohol and an alkyl aryl carbonate or a diaryl carbonate (in the case of the reaction of formula 1 or 2), or a dialkyl carbonate and an alkyl aryl carbonate (in the case of the reaction of formula 3 or 4). However, too high a concentration of these products is undesirable, because the reactions of formulae 1 to 4 involved in the process of the present invention are reversible and, therefore, too high a concentration of these products causes the rate of conversion of the feedstock to be lowered.

The ratio of the reactant to the starting material to be fed to the continuous multi-stage distillation column may vary depending on the type and quantity of the catalyst and the reaction conditions, but, in general, the molar ratio of the reactant to the starting material is preferably in the range of from 0.01 to 1000.

In the present invention, the starting material is reacted with the reactant in the presence of a catalyst within the continuous multi-stage distillation column, to thereby produce an aromatic carbonate corresponding to the starting material and the reactant as a desired product and produce an aliphatic alcohol [in the case of the reactions of formulae (1) and (2)] or a dialkyl carbonate [in the case of the reactions of formulae (3) and (4)] corresponding to the starting material and the reactant as a by-product. The desired product or the by-product, whichever is lower in boiling point, i.e., a low boiling point reaction product is continuously withdrawn in a gaseous form from the distillation column. In the reaction involved in the process of the present invention, the by-produced aliphatic alcohol or dialkyl carbonate is generally lower in boiling point than the desired aromatic carbonate and, hence, the by-product is continuously withdrawn in a gaseous form from the distillation column. In this case, the withdrawn gaseous product may be either the low boiling point by-product alone or a mixture of the by-product and the starting material and/or reactant. Further, the withdrawn gaseous product may contain an aromatic carbonate, which is a high boiling point product, in a small amount.

The outlet for withdrawing the gaseous material containing a low boiling point by-product from the continuous multi-stage distillation column can be provided at an appropriate position in the column except the column bottom. The concentration of the low boiling point by-product in the vapor phase, in general, increases in accordance with the distance from the column bottom. Therefore, the outlet for the gaseous material is preferably provided at a position above both of the positions from which the starting material and the reactant as feedstocks are fed, i.e., between the feeding positions and the column top or in the column top, and it is particularly preferred to provide the outlet in the column top.

The gaseous component withdrawn in this way is liquidfied by cooling or the like, and a portion of the resultant liquid may be returned to the upper portion of the distillation column to thereby effect the so-called reflux operation. When the reflux ratio is increased by conducting this reflux operation, the distillation efficiency of a low boiling point by-product into a vapor phase is increased, thereby advantageously increasing the concentration of the low boiling point by-product in the withdrawn gaseous component. However, too much an increase in the reflux ratio disadvantageously leads to an increase in the thermal energy required. Thus, the reflux ratio is generally chosen in the range of from 0 to 20, preferably from 0 to 10.

An aromatic carbonate which is the desired product produced by the method of the present invention is continuously withdrawn form as a high boiling point product in a liquid from the lower portion of the continuous multi-stage distillation column. In this instance, the withdrawn liquid material may be either an aromatic carbonate alone or a mixture of an aromatic carbonate and the starting material and/or reactant, and may contain a little amount of a low boiling point product. When a high boiling point catalyst soluble in a liquid phase is used, the catalyst is contained in this withdrawn liquid material The outlet for withdrawing a liquid material containing the desired product, i.e., an aromatic carbonate, from the continuous multi-stage distillation column, is provided in a lower portion of the column, in particular preferably at a bottom portion of the column. A portion of the liquid material withdrawn in this way may be recycled to a lower portion of the distillation column in a gaseous form or a gas-liquid mixture form by heating by means of a reboiler.

The amount of the catalyst to be used in the present invention varies depending on the type thereof, the type of the continuous multi-stage distillation column, the types and proportions of the starting material and the reactant, the reaction conditions, such as reaction temperature and reaction pressure, and the like. When the catalyst is continuously fed to the reaction zone of the continuous multi-stage distillation column, the catalyst is generally used in an amount of from 0.0001 to 50% by weight, based on the total weight of the starting material and the reactant constituting the feedstock. When a solid catalyst disposed in the continuous multi-stage distillation column is employed, the catalyst is preferably used in an amount of from 0.01 to 75% by volume, based on the volume of an empty distillation column.

In the present invention the reaction takes place within the continuous multi-stage distillation column in which the catalyst is present, and, therefore, the quantity of the reaction product generally depends on the amount of the hold-up liquid in the distillation column. That is, when the height and the diameter of a distillation column are not changed, a greater hold-up capacity is preferred because the greater the hold-up capacity, the longer the residence time of the liquid phase, that is, the time during which the reaction is effected. However, when the amount of the hold-up liquid is too large, the residence time becomes too long, so that side reactions and flooding are likely to occur. Accordingly, in the present invention the amount of the hold-up liquid of the distillation column varies depending on the distillation conditions and the type of the distillation column. Generally, however, the amount of the hold-up liquid is in the range of from 0.005 to 0.75 in terms of the volume ratio of the hold-up liquid to the empty continuous multi-stage distillation column.

In the present invention, the average residence time of the liquid phase in the continuous multi-stage distillation column depends on the reaction conditions, the type and inner structure (for example, the types of the plate and packing) of the continuous multi-stage distillation column, but is generally in the range of from 0.001 to 50 hr, preferably from 0.01 to 10 hr, more preferably from 0.05 to 2 hr.

The reaction temperature means the temperature of the inside of the continuous multi-stage distillation column. The reaction temperature varies depending on the types of the starting material and the reactant, but is generally chosen in the range of from 50° to 350° C., preferably from 100° to 280° C. The reaction pressure varies depending on the types of the starting material and reactant and the reaction temperature, and it may be any of a reduced pressure, an atmospheric pressure and a superatmospheric pressure. The pressure is generally in the range of from 0.1 mmHg to 200 kg/cm$^2$.

It is not always necessary to use a solvent in the present invention. For the purpose of facilitating the reaction operation, an appropriate inert solvent, such as ethers, aliphatic hydrocarbons, aromatic hydrocarbons, halogenated aliphatic hydrocarbons and halogenated aromatic hydrocarbons, may be used as a reaction solvent.

An inert gas, such as nitrogen, helium, argon and the like, may be present in the reaction system as a material inert to the reaction. Further, the above-mentioned inert gas and a reaction-inert low boiling point organic compound may be introduced in a gaseous form to the lower portion of the continuous multi-stage distillation column for the purpose of accelerating the distilling-off of a produced low boiling point by-product.

In order to explain the process of the present invention illustratively, a mode of the process using a single continuous multi-stage distillation column is described below. The present invention, however, is not restricted to the following mode of the process.

For example, as shown in FIG. 1, both a mixed feedstock comprised of a starting material and a reactant and a catalyst are continuously fed from feeding pipe 2 through preheater 5 to continuous multi-stage distillation column 1 provided with reboiler 10 and condenser 13, and the column bottom liquid is heated by reboiler 10, thereby effecting reaction and distillation. A liquid component containing an aromatic carbonate which is a high boiling point product produced in the presence of the catalyst within the continuous multi-stage distillation column, is continuously withdrawn from the lower portion of the column as column bottom liquid 19. A gaseous component containing a low boiling point product which is a by-product is continuously withdrawn as column top gas 12, and condensed by condenser 13, and then continuously withdrawn as column top liquid 16. A portion of the column top liquid may be refluxed to the upper portion of the continuous multi-stage distillation column from 15.

Figure 2:
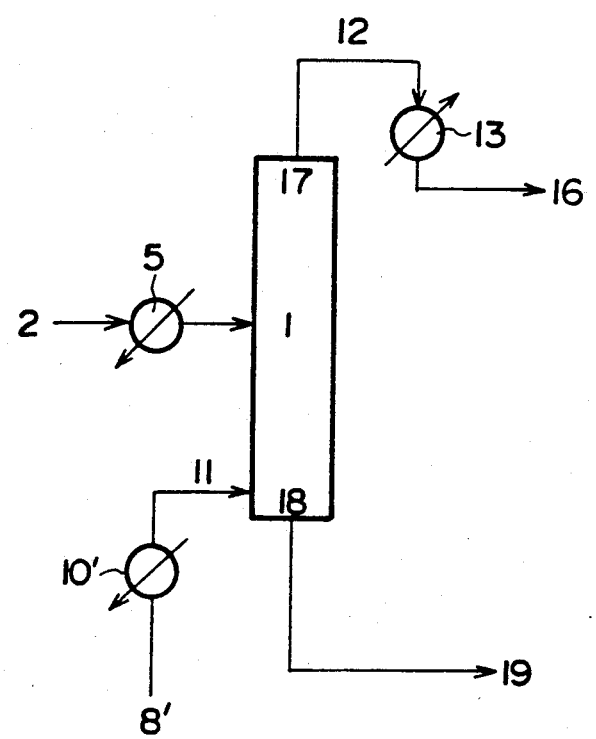

As shown in FIG. 2, both a mixed feedstock comprised of a starting material and a reactant and a catalyst are continuously fed from feeding pipe 2 through preheater 5 to continuous multi-stage distillation column 1, while the starting material or the reactant, whichever is lower in boiling point, is introduced from feeding pipe 8', evaporized by evaporator 10' and then continuously fed to the lower portion of continuous multi-stage distillation column 1, thereby effecting reaction and distillation. A liquid component containing an aromatic carbonate which is a high boiling point product produced in the presence of a catalyst within the continuous multi-stage distillation column, is continuously withdrawn as column bottom liquid 19 from the lower portion of the column. A gaseous component containing a low boiling point product which is a reaction by-product is continuously withdrawn as column top gas 12 and condensed by condenser 13, and then continuously withdrawn as column top liquid 16.

In the process of the present invention, a diaryl carbonate can be continuously produced with improved efficiency from a dialkyl carbonate and an aromatic hydroxy compound by the use of a plurality of, particularly two, continuous multi-stage distillation columns.

That is, in the second aspect of the present invention, there is provided a process according to the above-mentioned essential aspect of the present invention, wherein the continuous multi-stage distillation column is used as a first continuous multi-stage distillation column and has a second continuous multi-stage distillation column connected thereto and wherein the starting material and the reactant which are continuously fed to the first continuous multi-stage distillation column are, respectively, a dialkyl carbonate represented by

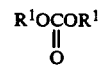

and an aromatic hydroxy compound represented by Ar¹OH, the aromatic carbonate or aromatic carbonate mixture contained in the produced high boiling point reaction mixture continuously withdrawn from the lower portion of the first distillation column is an alkyl aryl carbonate represented by

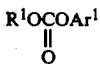

in which R¹ and Ar¹ are as defined above, and the by-product contained in the produced low boiling point reaction mixture continuously withdrawn from the upper portion of the first distillation column is an aliphatic alcohol represented by R¹OH, and which process further comprises continuously feeding the produced high boiling point reaction mixture continuously withdrawn from the lower portion of the first distillation column and containing the alkyl aryl carbonate represented by

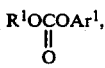

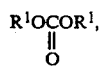

in which R¹ and Ar¹ are as defined above, and an alkyl aryl carbonate reactant represented by

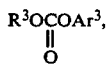

in which R³ is the same as or different from R¹ and Ar³ is the same as or different from Ar¹ with the proviso that R³ and Ar³ are, respectively, not simultaneously the same as R¹ and Ar¹, to the second continuous multi-stage distillation column to effect a liquid phase and/or gas-liquid phase transesterification reaction therebetween in the presence of a catalyst in the second distillation column, thereby producing a high boiling point reaction mixture containing a diaryl carbonate or diaryl carbonate mixture represented by

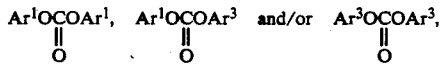

in which Ar¹ and Ar³ are as defined above, and a low boiling point reaction mixture containing a dialkyl carbonate by-product represented by

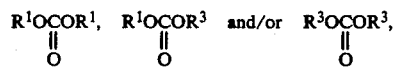

in which R¹ and R³ are as defined above, wherein the produced high boiling point reaction mixture is continuously withdrawn in a liquid form from a lower portion of the second distillation column and the low boiling point reaction mixture is continuously withdrawn in a gaseous form from an upper portion of the second distillation column by distillation.

In the above-mentioned method according to the second aspect of the present invention, it is preferred that the catalyst be a catalyst which is soluble in the liquid phase, being present in a state dissolved in the liquid phase within at least one of the first continuous multi-stage distillation column and the second continuous multi-stage distillation column, and/or that the catalyst be a solid catalyst which is substantially insoluble in the liquid phase, being disposed, in a state undissolved in the liquid phase, within at least one of the first continuous multi-stage distillation column and the second continuous multi-stage distillation column.

When R³ is the same as R¹ and Ar³ is different from Ar¹, it is desirable to recycle the low boiling point reaction mixture withdrawn from the upper portion of the second continuous multi-stage distillation column and containing a dialkyl carbonate represented by

to the first continuous multi-stage distillation column.

In the third aspect of the present invention, there is provided a process according to the above-mentioned essential aspect of the present invention, wherein the continuous multi-stage distillation column is used as a first continuous multi-stage distillation column and has a second continuous multi-stage distillation column connected thereto and wherein the starting material and the reactant which are continuously fed to the first continuous multi-stage distillation column are, respectively, a dialkyl carbonate represented by

and an aromatic hydroxy compound represented by Ar¹OH, the aromatic carbonate or aromatic carbonate mixture contained in the produced high boiling point reaction mixture continuously withdrawn from the lower portion of the first distillation column is an alkyl aryl carbonate represented by

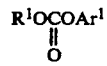

in which R¹ and Ar¹ are as defined above, and the by-product contained in the produced low boiling point reaction mixture continuously withdrawn from the upper portion of the first distillation column is an aliphatic alcohol represented by R¹OH, and which process further comprises continuously feeding the produced high boiling point reaction mixture continuously withdrawn from the lower portion of the first distillation column and containing the alkyl aryl carbonate represented by

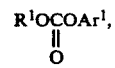

to the second continuous multi-stage distillation column to effect a liquid phase and/or gas-liquid phase, same species-intermolecular transesterification reaction between molecules of the alkyl aryl carbonate in the presence of a catalyst in the second distillation column, thereby producing a high boiling point reaction mixture containing a diaryl carbonate represented by

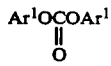

in which $Ar^1$ is as defined above, and a low boiling point reaction mixture containing a dialkyl carbonate by-product represented by

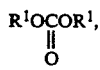

wherein the produced high boiling point reaction mixture is continuously withdrawn in a liquid form from a lower portion of the second continuous multi-stage distillation column and the low boiling point reaction mixture is continuously withdrawn by distillation in a gaseous form from an upper portion of the second continuous multi-stage distillation column.

In the above-mentioned third aspect as well, it is preferred to recycle the low boiling point reaction mixture withdrawn from the upper portion of the second continuous multi-stage distillation column and containing the dialkyl carbonate represented by

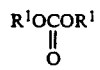

to the first continuous multi-stage distillation column.

In the method according to the above-mentioned third aspect, it is preferred that the catalyst be a catalyst which is soluble in the liquid phase, and is present in a state dissolved in the liquid phase within at least one of the first continuous multi-stage distillation column and the second continuous multi-stage distillation column, and/or that the catalyst be a solid catalyst which is substantially insoluble in the liquid phase, and is disposed, in a state undissolved in the liquid phase, within at least one of the first continuous multi-stage distillation column and the second continuous multi-stage distillation column.

When the catalyst is a catalyst which is soluble in the liquid phase, it is preferred that the catalyst be present in a state dissolved in the liquid phase within each of the first continuous multi-stage distillation column and the second continuous multi-stage distillation column, wherein the respective catalysts used in the first and second distillation columns are the same or different.

When a catalyst which is soluble in the liquid phase of such a reaction system is used, it is desirable to add a catalyst separation step so as to enable the catalyst to be recycled. That is, when part or all of the catalyst used in the first continuous multi-stage distillation column is present in a state dissolved in the liquid phase, it is preferred that, in feeding to the second continuous multi-stage distillation column the high boiling point reaction mixture withdrawn in liquid form from the lower portion of the first distillation column, the withdrawn high boiling point reaction mixture in liquid form be introduced to a first evaporator to effect a separation of the reaction mixture into an evaporated component containing the alkyl aryl carbonate represented by

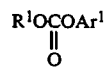

and a residual liquid having the catalyst dissolved therein, and that part or all of evaporated component be continuously fed to the second continuous multi-stage distillation column, while recycling part or all of the residual liquid containing the dissolved catalyst to the first continuous multi-stage distillation column.

The residual liquid separated by the first evaporator may contain a small amount of feedstock (a dialkyl carbonate and/or an aromatic hydroxy compound), an aromatic carbonate (an alkyl aryl carbonate and/or a diaryl carbonate) and other high boiling point by-products in addition to the catalyst component.

In the method according to this third aspect, when part or all of the catalyst present in the second continuous multi-stage distillation column is in a state dissolved in the liquid phase, it is preferred to introduce the high boiling point reaction mixture withdrawn in liquid form from the lower portion of the second distillation column to a second evaporator to effect a separation of the reaction mixture into an evaporated component containing a diaryl carbonate represented by

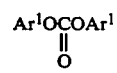

and a residual liquid having the catalyst dissolved therein, and thereafter to recycle part or all of the residual liquid containing the dissolved catalyst to the second continuous multi-stage distillation column.

The residual liquid separated by the second evaporator may contain a small amount of each of an aromatic hydroxy compound, an alkyl aryl carbonate, a diaryl carbonate and other high boiling point by-products, in addition to the catalyst component.

Such catalyst separation and recycling steps may be applied to either one or both of the high boiling point reaction mixture withdrawn in liquid form from the lower portion of the first continuous multi-stage distillation column and the high boiling point reaction mixture withdrawn in liquid form from the lower portion of the second continuous multi-stage distillation colum.

When other high boiling point by-products than the desired products are contained in these residual liquids containing the catalyst, part or all of the residual liquids may be taken-out and subjected to treatment for removing the high boiling point by-products prior to recycling the residual liquids.

In the process of the present invention, the high boiling point reaction mixture containing the desired aromatic carbonate which is withdrawn from the lower portion of the continuous multi-stage distillation column, can be subjected to the conventional method for separation and purification, such as distillation, crystallization and the like, to thereby isolate the desired aromatic carbonate.

BEST MODE FOR CARRYING OUT THE INVENTION

The present invention will be described in greater detail with reference to the following examples, which should not be construed as limiting the scope of the present invention.

EXAMPLE 1

A mixture of dimethyl carbonate, phenol and a catalyst was continuously fed in a liquid form to continuous multi-stage distillation column 1 at a position 1 m below the top thereof, which column was comprised of a packed column of 4 m in height and 3 inches in diameter and packed with a stainless steel-made Dixon packing (about 6 mm in diameter), from feeding pipe 2 through preheater 5 and conduit 6, as shown in FIG. 1. The thermal energy necessary for reaction and distillation was supplied by heating the liquid in the bottom of the distillation column with reboiler 10 and circulating the heated liquid through conduit 11. Reaction conditions are shown in Table 1. The liquid containing the catalyst and containing methyl phenyl carbonate and diphenyl carbonate as reaction products was continuously withdrawn from bottom 18 of the distillation column through conduits 8 and 19. Results of the reaction are shown in Table 1. The reaction liquid (reaction mixture) contained 0.02% by weight of anisol which was considered to have been formed by side reaction (decarboxylation reaction) of methyl phenyl carbonate. These results show that the selectivity for anisol relative to the phenol is 0.8%. Gas distilled from conduit 12 disposed at top 17 of the column was condensed by means of condenser 13. A portion of the resultant condensate was recycled into distillation column 1 through conduit 15, and the rest of the condensate was continuously withdrawn through conduit 16. From the condensate, methanol was obtained as a low boiling point reaction product.

COMPARATIVE EXAMPLE 1

Figure 6:
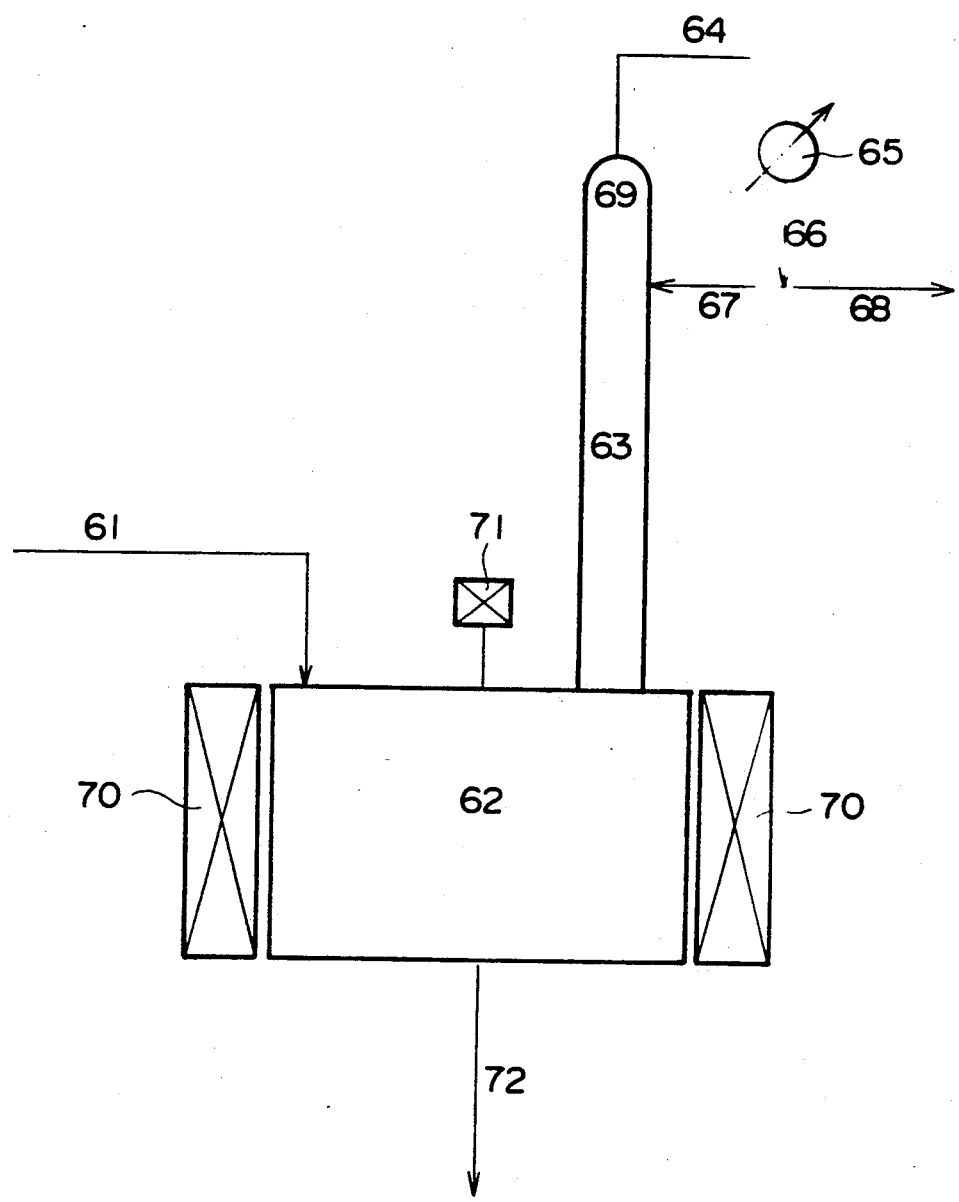
FIG. 6 is a diagram of a reactor apparatus for use in the conventional process described in Comparative Examples 1, 2 and 3.

12.6 kg of a mixture having the same composition as used in Example 1 was charged from feeding pipe 61 into autoclave type tank reactor 62 having a capacity of 15 liters and provided with distillation column 63 of 1 m in height and 1 inch in diameter [packed with a stainless steel-made Dixson packing (about 6 mm in diameter)] and stirrer 71 as shown in FIG. 6. Tank reactor 62 was heated by means of electric furnace 70, while stirring, so as to keep the temperature of the mixture constant at 204° C., thereby perform reaction. The gas distilled from top 69 of distillation column 63 was led through conduit 64 into condenser 65, in which condensation was effected. A portion of the resultant condensate was recycled through conduits 66 and 67, and the rest of the condensate was continuously withdrawn at a rate of 2.1 kg/hr through conduit 68. Reflux ratio was 0.8. At the time when 4.2 kg of condensate was withdrawn, tank reactor 62 was cooled and the reaction mixture was withdrawn through conduit 72. The quantity of the withdrawn liquid was 8.4 kg. The ratio of the quantity of the liquid remaining in the tank reactor to that charged into the tank reactor in this Comparative Example was the same as the ratio of the quantity of the column bottom liquid withdrawn through conduit 19 to the quantity of the liquid fed through conduit 6 in Example 1. The distillation rates of the distillates formed by condensing the gaseous components were also the same. Analyses showed that the reaction mixture contained 1.8% by weight of methyl phenyl carbonate, 0.01% by weight of diphenyl carbonate and 0.07% by weight of anisol. The amount of product obtained per kg of the reaction mixture and per hour was 9 g/kg·hr for methyl phenyl carbonate and 0.05 g/kg·hr for diphenyl carbonate. The selectivity of the aromatic carbonate based on the phenol converted was 94% for methyl phenyl carbonate and 1% for diphenyl carbonate. The selectivity of the by-produced anisol based on the phenol converted was 5%. When substantially the same reaction as mentioned above was conducted for 4 hr, the selectivity of the by-produced anisol changed to 7%.

From the results of Example 1, in which the production rate of methyl phenyl carbonate was 34 g/kg·hr (97% in selectivity), that of diphenyl carbonate 0.5 g/kg·hr (2% in selectivity) and the selectivity of the by-produced anisol was 0.8% (constant independently of the lapse of the reaction time), it is apparent that the method of the present invention is an excellent method which can produce an aromatic carbonate not only at a high reaction rate in a high yield (high productivity per unit time) with a high selectivity but also in a continuous fashion, as compared with the method (Comparative Example 1) in which a batch type tank reactor provided only with a distillation column at an upper portion thereof is used.

EXAMPLES 2 to 4

Using the same apparatus as in Example 1, the reaction was carried out under the reaction conditions shown in Table 1. Results are shown in Table 1.

EXAMPLE 5

A mixture of dimethyl carbonate, phenol and a catalyst was continuously fed in a liquid form to continuous multi-stage distillation column 1 at a position 1 m below the top thereof, which column was comprised of a packed column of 4 m in height and 3 inches in diameter and packed with a stainless steel-made Dixon packing (about 6 mm in diameter), from feeding pipe 2 through preheater 5, as shown in FIG. 2. Simultaneously, dimethyl carbonate (which may contain a small amount of phenol) was introduced from feeding pipe 8' so as to continuously feed the same through evaporator 10' into the bottom portion of distillation column 1 in a gaseous form. Reaction conditions are shown in Table 2. High boiling point reaction products containing methyl phenyl carbonate and diphenyl carbonate as reaction products were continuously withdrawn from the bottom of the column through conduit 19. Gas distilled from the top of the column was led through conduit 12 into condenser 13 in which the gas was condensed. Methanol as a low boiling point product, was obtained from the liquid which was continuously withdrawn through conduit 16. Results of the reaction are shown in Table 2.

EXAMPLES 6 to 9

Using the same apparatus as in Example 5, the reaction was carried out under the reaction conditions shown in Table 2. Results are shown in Table 2.

EXAMPLE 10

A reaction was carried out in substantially the same manner as described in Example 5, except that a 20-stage plate column of 6 m in height and 10 inches in diameter provided with sieve trays was used instead of a packed column as a continuous multi-stage distillation column as shown in FIG. 2 and the reaction was conducted under the reaction conditions indicated in Table 2. The feedstock mixture and catalyst to be introduced from feeding pipe 2 through preheater 5 were continuously fed to the column at a position 0.5 m below the top thereof. Results are shown in Table 2.

EXAMPLE 11

A reaction was continuously carried out in substantially the same manner as described in Example 1 except that a mixture of methyl phenyl carbonate and a catalyst was continuously fed instead of a mixture of dimethyl carbonate, phenol and a catalyst, and that the reaction was conducted under the reaction conditions indicated in Table 3. As a consequence of the reaction, from column bottom 18 of the continuous multi-stage distillation column, a column bottom liquid containing catalyst components and diphenyl carbonate as a desired product was continuously withdrawn through conduit 19. A condensate of gaseous components from the column top was continuously withdrawn through conduit 16. This condensate contained a small amount of anisol, and the other component of the condensate was dimethyl carbonate as a low boiling point reaction product. The selectivity of the by-produced anisol based on the methyl phenyl carbonate converted was 0.7%. Results of the reaction are shown in Table 3.

COMPARATIVE EXAMPLE 2

To the same apparatus used in Comparative Example 1, 12.6 kg of a mixture of the same composition as used in Example 11 was charged through conduit 61. A reaction was conducted in substantially the same manner as described in Comparative Example 1, except that the liquid temperature was maintained at 195° C. during the reaction by heating tank reactor 62 by means of electric furnace 70 while stirring, that a condensate of gaseous components from the column top was continuously withdrawn through conduit 68 at a rate of 1.0 kg/hr, and the reflux ratio was 2.1. The reaction was carried out for 3 hours from the start of the withdrawal, and 3.0 kg of condensate was withdrawn. After cooling tank reactor 62, the reaction mixture was withdrawn through conduit 72, which weighed 9.6 kg. The ratio of the amount of withdrawn condensate to that of withdrawn liquid from the tank reactor in this comparative example was the same as the ratio of the amount of withdrawn condensate from the column top to that of withdrawn liquid from the column bottom in Example 11. Analyses showed that the reaction mixture contained 67.3% by weight of diphenyl carbonate. The amount of diphenyl carbonate produced per kg of the reaction mixture and per hour was 224 g/kg·hr. The selectivity of the diphenyl carbonate based on the methyl phenyl carbonate converted was 95%. By the analysis of the condensate from the column top, by-produced anisol was detected. The selectivity of the anisol based on the methyl phenyl carbonate converted was 5%. Comparison of this result with the result obtained in Example 11 shows that diaryl carbonate can be produced at a higher yield and with a higher selectivity according to the process of the present invention.

EXAMPLES 12 to 17

Using the same apparatus used in Example 11, the experiment was carried out under the reaction conditions indicated in Table 3. Results are shown in Table 3.

EXAMPLE 18

Using the same apparatus used in Example 5, a reaction was carried out in substantially the same manner as described in Example 5 by continuously feeding a mixture of methyl phenyl carbonate and a catalyst from feeding pipe 2 through preheater 5, and further introducing methyl phenyl carbonate from feeding pipe 8, so as to continuously feed through evaporator 10' and conduit 11 to the column bottom of distillation column 1 in a gaseous form. Reaction conditions are indicated in Table 4. A liquid containing diphenyl carbonate as a reaction product was continuously withdrawn from the bottom of the continuous multi-stage distillation column. Further, the gas distilled from the top of the column was condensed by means of condenser 13, and continuously withdrawn through conduit 16. From the thus obtained condensate, dimethyl carbonate was obtained as a low boiling point reaction product. Results are shown in Table 4.

EXAMPLES 19 to 20

Using the same apparatus as used in Example 18, a reaction was carried out under the reaction conditions indicated in Table 4. Results are shown in Table 4.

In Example 19, the reaction was carried out by introducing phenol from feeding pipe 8'. As a result, methanol and dimethyl carbonate were contained in the condensate from the top of the column.

EXAMPLE 21

A reaction was carried out in substantially the same manner as described in Example 18, except that the same plate column used in Example 10 was used as a continuous multi-stage distillation column, that a feedstock and a catalyst were continuously fed into the column at a position 0.5 m below the top thereof, and the reaction conditions were as shown in Table 4. Results are shown in Table 4.

EXAMPLE 22

Preparation of Catalyst 20 kg of diphenyl carbonate and 4 kg of lead monoxide were heated at 180° C. for 5 hours to evolve carbon dioxide gas. Then, the most part of the remaining diphenyl carbonate was distilled off under a pressure of 10 mmHg, and the resultant product was allowed to cool down in a nitrogen atmosphere, thereby obtaining a catalyst (Catalyst A).

Production of Diphenyl Carbonate

Figure 3:
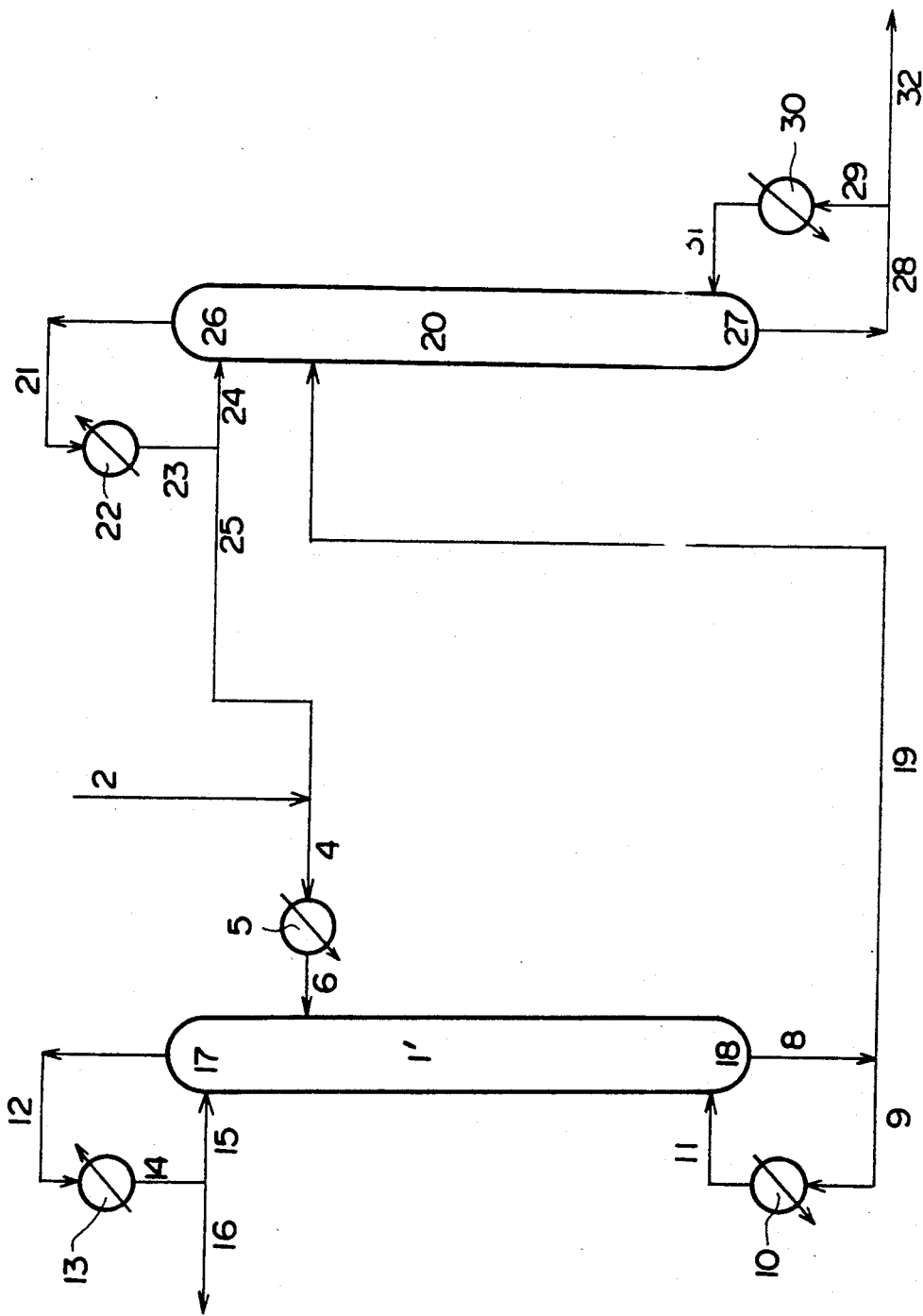

An apparatus comprising two continuous multi-stage distillation columns as shown in FIG. 3 was employed. Reaction was performed by continuously feeding in a liquid form a mixture of dimethyl carbonate, phenol and Catalyst A to first continuous multi-stage distillation column 1' at a position 1 m below top 17 thereof, which column was comprised of a packed column of 4 m in height and 3 inches in diameter and packed with stainless steel-made Dixon packing (diameter: about 6 mm), from material feeding pipe 2 through conduit 4, preheater 5 and conduit 6, thereby allowing the mixture to flow down the inside of the first continuous multi-stage distillation column. The thermal energy necessary for reaction and distillation was supplied by circulating the column bottom liquid through conduits 8 and 9, reboiler 10 where heating was effected and conduit 11. The gas continuously distilled from column top 17 was led through conduit 12 to condenser 13 where the gas was condensed. A portion of the resultant condensate was recycled to first continuous multi-stage distillation column 1, through conduits 14 and 15 and the rest of the condensate was continuously withdrawn through conduit 16. From the withdrawn condensate, a low boiling point component containing methanol which was a low boiling point reaction product was obtained. A high boiling point component containing the catalyst component and methyl phenyl carbonate was continuously withdrawn from column bottom 18 through conduits 8 and 19.

Next, reaction was performed by continuously feeding in a liquid form the liquid withdrawn from the bottom of the first reaction distillation column to second continuous multi-stage distillation column 20 at a position 1 m below column top 26, which column was comprised of a packed column of 4 m in height and 3 inches in diatemer and packed with stainless steel-made Dixon packing (diameter: about 6 mm), through conduit 19, thereby allowing the liquid to flown down the inside of the second continuous multi-stage distillation column. The thermal energy necessary for distillation was supplied by circulating the column bottom liquid through conduits 28 and 29, reboiler 30 where heating was effected, and conduit 31. In this second continuous multi-stage distillation column, the catalyst which had been used in the first continuous multi-stage distillation column for the formation of an alkyl aryl carbonate and which had not been separated, as such, was utilized as a catalyst for the formation of a diaryl carbonate. The gas containing dimethyl carbonate, which was continuously distilled from column top 26, was led through conduit 21 to condenser 22 where the gas was condensed. A portion of the condensate was recycled to second continuous multi-stage distillation column 20 through conduits 23 and 24. The rest of the condensate was continuously withdrawn through conduits 23 and 25 and recycled to first continuous multi-stage distillation column 1' through conduit 4, preheater 5 and conduit 6. A high boiling point component containing the catalyst and diphenyl carbonate was continuously withdrawn from bottom 27 of second continuous multi-stage distillation column 20 through conduits 28 and 32. The conditions for reaction and the results attained after the steady state, are shown in Table 5.

EXAMPLE 23

Preparation of Catalyst 20 kg of phenol and 4 kg of dibutyltin oxide were heated at 180° C. for 10 hours while distilling off water being formed together with phenol. Then, the most part of the remaining phenol was distilled off under atmospheric pressure, and the resultant product was allowed to cool in a nitrogen atmosphere, thereby obtaining a catalyst (Catalyst B).

Production of Diphenyl Carbonate

Using the same apparatus as in Example 22, substantially the same procedure as in Example 22 was performed except that Catalyst B was employed instead of Catalyst A. The reaction conditions and the results attained after the steady state had been reached, are shown in Table 5.

EXAMPLE 24

Preparation of Catalyst 20 kg of methyl phenyl carbonate and 4 kg of plumbous acetate were heated at 180° C. for 10 hours. Then, the most part of the remaining methyl phenyl carbonate was distilled off under a pressure of 100 mmHg, and the resultant product was allowed to cool in a nitrogen atmosphere, thereby obtaining a catalyst (Catalyst C).

Production of Diphenyl Carbonate

Figure 4:
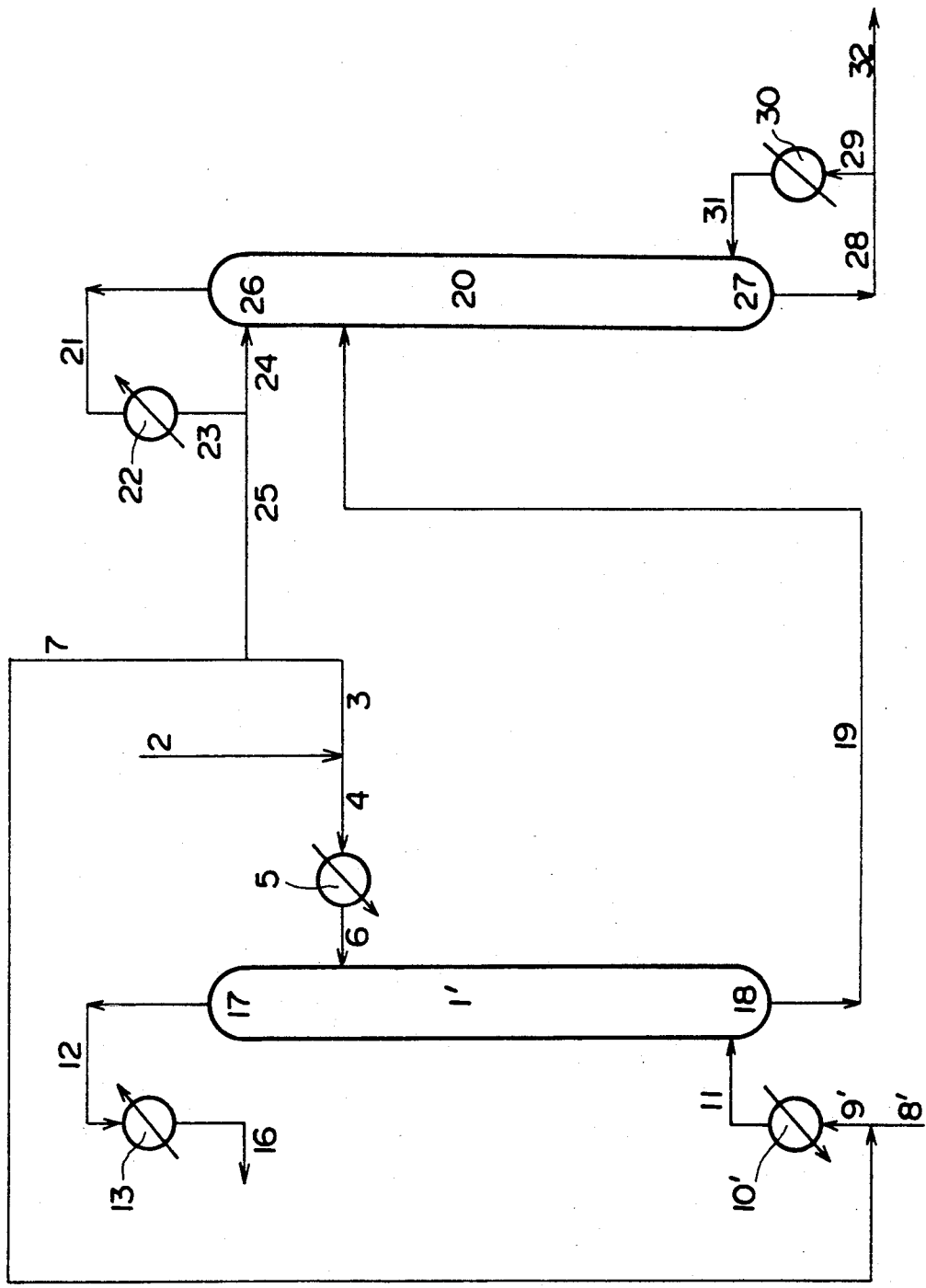

The apparatus shown in FIG. 4 was employed. Reaction was performed by continuously feeding in a liquid form a mixture of dimethyl carbonate, phenol and Catalyst C to first continuous multi-stage distillation column 1' at a position 1 m below column top 17, which column was comprised of a packed column of 4 m in height and 3 inches in diameter and packed with stainless steel-made Dixon packing (diameter: about 6 mm), from material feeding pipe 2 through conduit 4, preheater 5 and conduit 6, thereby allowing the mixture to flow down the inside of first continuous multi-stage distillation column 1'. The thermal energy necessary for reaction and distillation was supplied by circulating through conduit 9', evaporator 10' where heating was effected and conduit 11, a portion of the dimethyl carbonate-containing low boiling point component returned from second continuous multi-stage distillation column 20 described below, together with fresh dimethyl carbonate fed from feeding pipe 8'. The gas distilled from column top 17 was led through conduit 12 to condenser 13 where the gas was condensed, and the condensate was continuously withdrawn through conduit 16. From the condensate, a low boiling point reaction mixture containing methanol which was a reaction product was obtained. A high boiling point reaction mixture containing methyl phenyl carbonate and catalyst components was continuously withdrawn from column bottom 18 through conduit 19.

Next, a reaction was performed by continuously feeding in a liquid form the liquid withdrawn from the bottom of first continuous multi-stage distillation column 1' to second continuous multi-stage distillation column 20 at a position 1 m below column top 26, which column was comprised of a packed column of 4 m in height and 3 inches in diameter and packed with stainless steel-made Dixon packing (diameter: about 6 mm), through conduit 19, thereby allowing the liquid to flow down the inside of second continuous multi-stage distillation column 20. The thermal energy necessary for distillation was supplied by circulating the column bottom liquid through conduits 28 and 29, reboiler 30 where heating was effected, and conduit 31. In this second continuous multi-stage distillation column 20, the catalyst used in first continuous multi-stage distillation column 1' for the formation of an alkyl aryl carbonate and which had not been separated, was utilized as it was, as a catalyst for the formation of a diaryl carbonate. The gas containing dimethyl carbonate, which was continuously distilled from column top 26, was led through conduit 21 to condenser 22 where the gas was condensed. A portion of the condensate was recycled to second continuous multi-stage distillation column 20 through conduits 23 and 24. The rest of the condensate was continuously withdrawn through conduits 23 and 25 and recycled to first continuous multi-stage distillation column 1' through conduits 3 and 4, preheater 5 and conduit 6. A portion of the condensate withdrawn through conduit 25 was recycled to the lower portion of continuous multi-stage distillation column 1' through conduit 7 and evaporator 10'. A high boiling point reaction mixture containing the catalyst component and diphenyl carbonate was continuously withdrawn from bottom 27 of second continuous multi-stage distillation column 20 through conduits 28 and 32. The reaction conditions and the results attained after the steady state, are shown in Table 5.

EXAMPLE 25

Using the same apparatus as in Example 24, substantially the same procedure as in Example 24 was performed except that p-cresol was employed instead of phenol. The reaction conditions and the results attained after the steady state, are shown in Table 5.

EXAMPLE 26

Using the same apparatus as in Example 24, substantially the same procedure as in Example 24 was performed except that diethyl carbonate was employed instead of dimethyl carbonate. The reaction conditions and the results attained after the steady state, are shown in Table 5.

EXAMPLE 27

Preparation of Catalyst 15 kg of phenol, 5 kg of methyl phenyl carbonate, and 4 kg of dibutyltin oxide were heated at 180° C. for 10 hours while distilling off water being formed together with phenol. Then, the most part of each of the remaining phenol and the remaining methyl phenyl carbonate was distilled off under atmospheric pressure, and the resultant product was allowed to cool in a nitrogen atmosphere, thereby obtaining a catalyst (Catalyst D).

Production of Diphenyl Carbonate

Using the same apparatus as in Example 24, substantially the same procedure as in Example 24 was performed except that Catalyst D was employed instead of Catalyst C. The reaction conditions and the results attained after the steady state, are shown in Table 5.

EXAMPLE 28

Using the same apparatus as in Example 24, substantially the same procedure as in Example 24 was performed except that tetraphenoxy titanium was employed instead of Catalyst C. The reaction conditions and the results attained after the steady state, are shown in Table 5.

EXAMPLE 29

Preparation of Catalyst 20 kg of phenol and 4 kg of lead monoxide were heated at 180° C. for 10 hours while distilling off water being formed together with phenol, thereby obtaining a catalyst (Catalyst E).

Production of Diphenyl Carbonate

Figure 5:
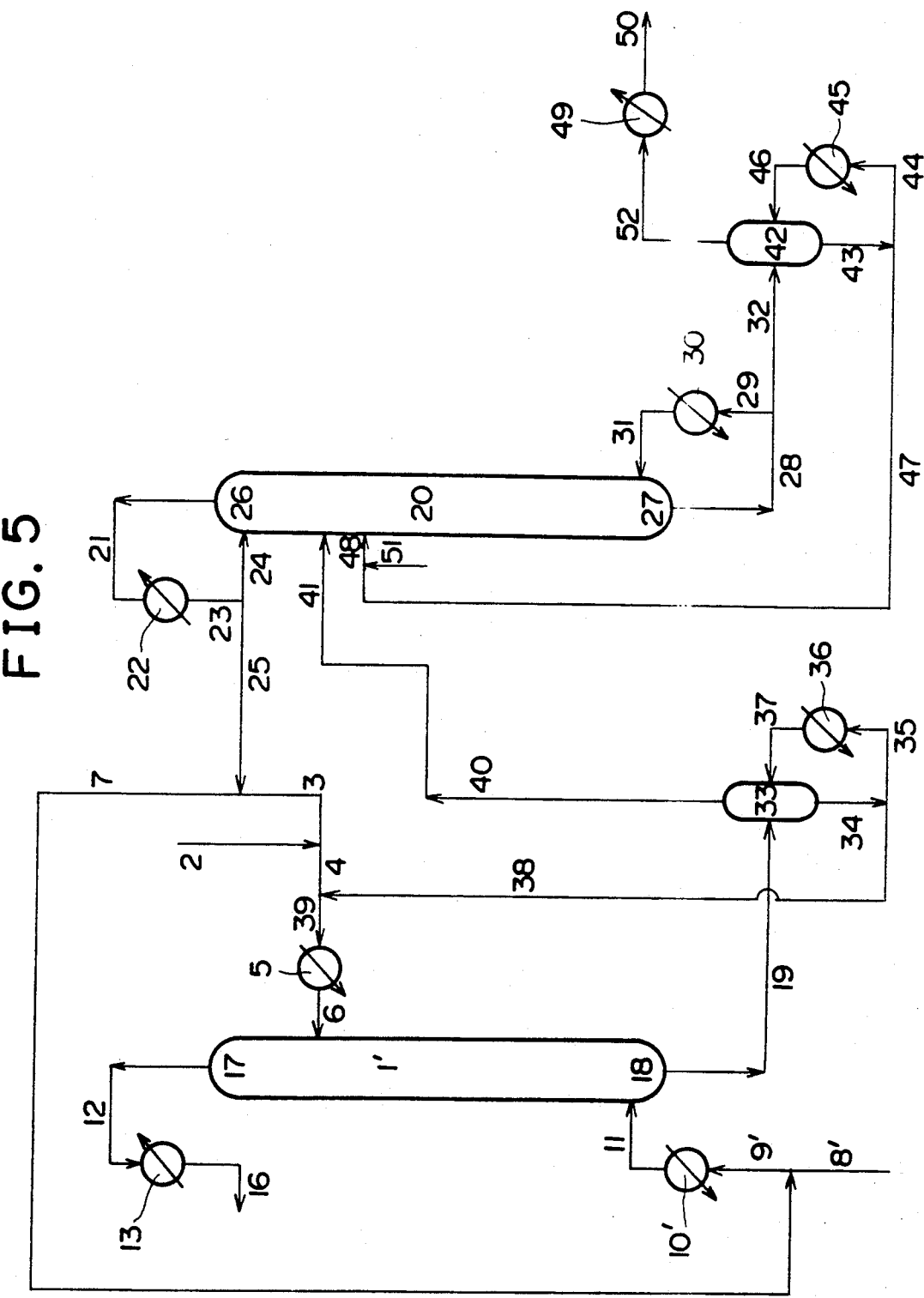

An apparatus as shown in FIG. 5 was employed. Reaction was performed by continuously feeding in a liquid form a mixture of dimethyl carbonate, phenol and Catalyst E to first continuous multi-stage distillation column 1' at a position 0.5 m below column top 17, which column was comprised of a 20-plate column of 6 m in height and 10 inches in diameter and provided with sieve trays, from material feeding pipe 2 through conduits 4 and 39, preheater 5 and conduit 6, thereby allowing the mixture to flow down the inside of the first continuous multi-stage distillation column 1'. The thermal energy necessary for reaction and distillation was supplied by heating with evaporator 10' a portion of the low boiling point reaction mixture returned from second continuous multi-stage distillation column 20 described below through conduits 24, 25 and 7, together with fresh dimethyl carbonate fed from feeding pipe 8' and through conduit 9', and circulating the heated mixture through conduit 11. The gas distilled from column top 17 was led through conduit 12 to condenser 13 where the gas was condensed, and the condensate was continuously withdrawn through conduit 16. From the withdrawn condensate, a low boiling point reaction mixture containing methanol which was a low boiling point reaction product was obtained. The reaction mixture continuously withdrawn from column bottom 18 was introduced into evaporator 33 through conduit 19. The residual liquid in evaporator 33 containing the catalyst for the formation of methyl phenyl carbonate was returned from the bottom of evaporator 33 to first continuous multi-stage distillation column 1' through conduits 34, 38 and 39, preheater 5 and conduit 6. The feeding of catalyst E through conduit 2 was stopped at the time when the concentration of the catalyst being recycled had reached a predetermined value.

The vaporized product containing methyl phenyl carbonate generated in evaporator 33 by circulating a portion of the residual liquid flowing out of evaporator 33 through conduit 34, to evaporator 33 through conduit 35, reboiler 36 and conduit 37, was continuously fed to second continuous multi-stage distillation column 20 comprised of a plate column of 6 m in height and 10 inches in diameter and provided with a 20-stage sieve tray, through conduit 40 and from feeding pipe 41 positioned 1.5 m below column top 26. The catalyst (Catalyst E) for the formation of diaryl carbonate was continuously fed in a liquid form to second continuous multi-stage distillation column 20 through conduit 51 and from feeding pipe 48 positioned 1.5 m below the column top. The most part of the gaseous methyl phenyl carbonate fed to second continuous multi-stage distillation column 20 is liquefied in the column and the resultant liquid flows down the inside of the column together with the catalyst, thereby effecting the reaction. The thermal energy necessary for reaction and distillation was supplied by circulating the column bottom liquid from column 20 through conduits 28 and 29, reboiler 30 where the liquid was heated, and conduit 31 so that the liquid was returned to column 20. A low boiling point reaction mixture containing dimethyl carbonate and continuously distilled from column top 26 was led through conduit 21 to condenser 22 where condensation was effected. A portion of the resultant condensate was recycled to second continuous multi-stage distillation column 20 through conduits 23 and 24. The rest of the condensate was continuously withdrawn through conduits 23 and 25 and recycled to first continuous multi-stage distillation column 1' through conduits 3, 4 and 39, preheater 5 and conduit 6. A portion of the condensate continuously withdrawn through conduit 25 was recycled to the lower portion of first continuous multi-stage distillation column 1' through conduits 7 and 9', evaporator 10' and conduit 11. A high boiling point reaction mixture containing the catalyst and diphenyl carbonate and which was continuously withdrawn from bottom 27 of second continuous multi-stage distillation column 20 was introduced to second evaporator 42 through conduits 28 and 32. The vaporized product generated in evaporator 42 by circulating a portion of the residual liquid flowing out of evaporator 42 through conduit 43, to evaporator 42 through conduit 44, reboiler 45 and conduit 46, was continuously withdrawn in a liquid form through conduit 52, condenser 49 and conduit 50. The vaporized product contained diphenyl carbonate as the main ingredient. The residual liquid in evaporator 42 containing the catalyst for the formation of diaryl carbonate was recycled from the bottom of evaporator 42 to second continuous multi-stage distillation column 20 through conduits 43, 47 and 48. The feeding of catalyst E through conduit 51 was stopped when the concentration of the catalyst being recycled had reached a predetermined value. The flow rates and the compositions at portions of the apparatus are shown in Table 6. The reaction conditions and the results attained after the steady state had been reached, are shown in Table 7.

EXAMPLE 30

Preparation of Catalyst 5 kg of γ-alumina (manufactured and sold by Nikki Co., Japan; Product No. 611N) was packed into a cylinder made of quartz glass (length: 100 cm; diameter: 10 cm) and the cylinder was placed in a tubular furnace. The inside of the furnace was flushed with nitrogen and the furnace was heated at 200° C. for 5 hours, thereby drying the γ-alumina. Next, into the cylinder, which had been heated to 200° C., was introduced a (20 wt %) benzene solution of tetramethoxy silane for 10 hours at a flow rate of 50 ml/hr, thereby treating the γ-alumina. The thus treated product was allowed to cool down in a nitrogen atmosphere, thereby obtaining a catalyst (Catalyst F).

Production of Diphenyl Carbonate

Substantially the same procedure as in Example 24 was performed except that a packed column of 2 m in height and 1.5 inches in diameter and packed with Catalyst F was employed as each of the first continuous multi-stage distillation column and the second continuous multi-stage distillation column. The reaction conditions and the results attained after the steady state had been reached, are shown in Table 5.

COMPARATIVE EXAMPLE 3

Into the same apparatus as used in Comparative Example 1, which apparatus is shown in FIG. 6, charged through conduit 61 was 12.8 kg of a mixture of the same composition as used in Example 23. Reaction was effected in substantially the same manner as in Comparative Example 1 by heating tank reactor 62 by means of electric furnace 70, while stirring, except that the temperature of the reaction mixture was kept constant at 202° C. and that the condensate was continuously withdrawn through conduit 68 at a rate of 1.0 kg/hr. At the time when the amount of the condensate withdrawn from the reactor had become 12.1 kg, tank reactor 62 was cooled down and the reaction mixture was withdrawn through conduit 72. The quantity of the withdrawn reaction mixture was 0.7 kg. The ratio of the quantity of the reaction mixture remaining in the tank reactor to that charged into the tank reactor in this Comparative Example 3 was the same as the ratio of the quantity of the column bottom liquid withdrawn through conduit 28 to the quantity of the liquid fed through conduit 6 in Example 23. Analysis showed that the reaction mixture contained 14.0% by weight of formed diphenyl carbonate. The amount of diphenyl carbonate formed per kg of the reaction mixture and per hour was 12 g/kg·hr. The selectivity of the diphenyl carbonate based on the phenol converted was 83%. Analysis of the column top condensate showed that anisole had been by-produced with a selectivity of 8% based on the phenol converted.

Comparison of the above results with the results of Example 23 (the production rate of diphenyl carbonate: 524 g/kg·hr; selectivity: 95%) shows that the method of the present invention is an excellent method which can produce diphenyl carbonate not only at a high reaction rate with a high selectivity in a high yield but also in a continuous fashion.

TABLE 1

| Example | Feed liquid from feeding pipe 2 | | | | | Reaction conditions | | | Condensate (conduit 16) Flow rate kg/hr | Column bottom liquid (conduit 19) | | Aromatic carbonate | |
|---|---|---|---|---|---|---|---|---|---|---|---|---|---|
| | Flow rate kg/hr | Composition | | | | Temperature at column bottom °C. | Pressure at column top kg/cm² | Reflux ratio | | Flow rate kg/hr | Composition Type (wt %) | Amount of product Type (g/kg · hr) | Selectivity Type (%) |
| | | Dialkyl carbonate Type (wt %) | Aromatic hydroxy compound Type (wt %) | Catalyst Type (mmol/kg) | | | | | | | | | |
| 1 | 6.3 | DMC (73.2) | PhOH (26.8) | Pb(OPh)₂ (6.3) | | 204 | 8 | 0.8 | 2.1 | 4.2 | MPC (3.4) DPC (0.05) | MPC (34) DPC (0.5) | MPC (97) DPC (2) |
| 2 | 4.2 | DMC (57.7) | p-cresol (42.3) | Pb(OPh)₂ (9.5) | | 203 | 8 | 1.5 | 1.3 | 2.9 | MTC (4.2) DTC (0.07) | MTC (42) DTC (0.7) | MTC (97) DTC (2) |
| 3 | 4.5 | DEC (56.3) | PhOH (43.7) | Pb(OPh)₂ (8.7) | | 203 | 8 | 1.2 | 1.3 | 3.2 | EPC (4.2) DPC (0.09) | EPC (42) DPC (0.9) | EPC (96) DPC (3) |
| 4 | 3.4 | DMC (66.3) | PhOH (33.7) | Ti(OPh)₄ (13.5) | | 201 | 8 | 1.0 | 1.1 | 2.3 | MPC (5.0) DPC | MPC (50) DPC | MPC (98) DPC |

TABLE 1-continued

| | Feed liquid from feeding pipe 2 | | | Reaction conditions | | | Condensate | Column bottom liquid | | Aromatic carbonate | |
|---|---|---|---|---|---|---|---|---|---|---|---|
| | | Composition | | | | | (conduit 16) | (conduit 19) | | Amount | |
| | | | Aromatic | | Temperature at | Pressure at | | | | | |
| | | Dialkyl | hydroxy | | column | column | | | Composition | of | Selectivity |
| Example | Flow rate kg/hr | carbonate Type (wt %) | compound Type (wt %) | Catalyst Type (mmol/kg) | bottom °C. | top kg/cm² | Reflux ratio | Flow rate kg/hr | Flow rate kg/hr | Type (wt %) | product Type (g/kg · hr) | Type (%) |
| | | | | | | | | | | (0.04) | (0.4) | (1) |

<Description of symbols>
DMC: dimethyl carbonate
DEC: diethyl carbonate
PhOH: phenol
Pb(OPh)$_2$: diphenoxy lead
Ti(OPh)$_4$: tetraphenoxy titanium
MPC: methyl phenyl carbonate
MTC: methyl tolyl carbonate
EPC: ethyl phenyl carbonate
DPC: diphenyl carbonate
DTC: ditolyl carbonate
wt %: % by weight
(Note)
1. The catalyst concentration was determined by means of an ICP (inductively coupled plasma emission spectral analyzer).
2. The amount of the produced aromatic carbonate is expressed in terms of grams of the product per kg of the column bottom liquid and per hour.
3. The selectivity of the aromatic carbonate is calculated, based on the aromatic hydroxy compound, a raw material, converted.

TABLE 2

| | Feed liquid from feeding pipe 2 | | | | Feed liquid from feeding pipe 8' | | |
|---|---|---|---|---|---|---|---|
| | | Composition | | | | Composition | |
| | Flow rate | Dialkyl carbonate | Aromatic hydroxy compound | Catalyst Type | Flow rate | Dialkyl carbonate | Aromatic hydroxy compound |
| Example | kg/hr | Type (wt %) | Type (wt %) | (mmol/kg) | kg/hr | Type (wt %) | Type (wt %) |
| 5 | 2.2 | DMC (54.7) | PhOH (45.3) | Pb(OPh)$_2$ (9.1) | 3.1 | DMC (88.8) | PhOH (11.2) |
| 6 | 2.2 | DMC (53.6) | PhOH (46.4) | Pb(OPh)$_2$ (9.0) | 3.1 | DMC (100) | — |
| 7 | 2.4 | DMC (45.3) | PhOH (54.7) | Bu$_2$SnO (8.3) | 3.0 | DMC (85.5) | PhOH (14.5) |
| 8 | 2.1 | DMC (57.7) | p-cresol (42.3) | Pb(OPh)$_2$ (9.5) | 2.2 | DMC (95.5) | p-cresol (4.5) |
| 9 | 2.3 | DEC (56.3) | PhOH (43.7) | Pb(OPh)$_2$ (8.7) | 2.2 | DEC (100) | — |
| 10 | 24.5 | DMC (54.2) | PhOH (45.8) | Pb(OPh)$_2$ (40) | 46.2 | DMC (86.5) | PhOH (13.5) |

| | Reaction conditions | | | Condensate | Column bottom liquid | | Aromatic carbonate | |
|---|---|---|---|---|---|---|---|---|
| | Temperature at column | Pressure at column | | (conduit 16) | (conduit 19) | | Amount of | |
| Example | bottom °C. | top kg/cm² | Reflux ratio | Flow rate kg/hr | Flow rate kg/hr | Composition Type (wt %) | product Type (g/kg · hr) | Selectivity Type (%) |
| 5 | 205 | 8 | 0 | 2.3 | 3.0 | MPC (8.7) DPC (0.13) | MPC (87) DPC (1.3) | MPC (97) DPC (2) |
| 6 | 205 | 8 | 0 | 2.4 | 2.9 | MPC (9.3) DPC (0.13) | MPC (93) DPC (1.3) | MPC (97) DPC (2) |
| 7 | 205 | 8 | 0 | 2.1 | 3.3 | MPC (6.8) DPC (0.06) | MPC (68) DPC (0.6) | MPC (98) DPC (1) |
| 8 | 203 | 8 | 0 | 1.4 | 2.9 | MTC (7.2) DTC (0.1) | MTC (72) DTC (1) | MTC (97) DTC (2) |
| 9 | 203 | 8 | 0 | 1.3 | 3.2 | EPC (7.1) DPC (0.1) | EPC (71) DPC (1) | EPC (97) DPC (2) |
| 10 | 203 | 8 | 0 | 36.6 | 34.1 | MPC (15.7) DPC | MPC (157) DPC | MPC (97) DPC |

TABLE 2-continued

|  |  |  |
|---|---|---|
| (0.2) | (2) | (2) |

<Description of symbols>
DMC: dimethyl carbonate
DEC: diethyl carbonate
PhOH: phenol
Pb(OPh)$_2$: diphenoxy lead
Bu$_2$SnO: dibutyl tin oxide
MPC: methyl phenyl carbonate
MTC: methyl tolyl carbonate
EPC: ethyl phenyl carbonate
DPC: diphenyl carbonate
DTC: ditolyl carbonate
wt %: % by weight
(Note)
1. The catalyst concentration was determined by means of an ICP (inductively coupled plasma emission spectral analyzer).
2. The amount of the produced aromatic carbonate is expressed in terms of grams of the product per kg of the column bottom liquid and per hour.
3. The selectivity of the aromatic carbonate is calculated, based on the aromatic hydroxy compound, a raw material, converted.

TABLE 3

| Example | Feed liquid from Feeding pipe 2 | | | Reaction conditions | | | Condensate (conduit 16) Flow rate kg/hr | Column bottom liquid (conduit 19) | | Diaryl carbonate | | |
|---|---|---|---|---|---|---|---|---|---|---|---|---|
|  | Flow rate kg/hr | Alkyl aryl carbonate Type (wt %) | Catalyst Type (mmol/kg) | Temperature at column bottom °C. | Pressure at column top mmHg | Reflux ratio |  | Flow rate kg/hr | Composition Type (wt %) | Amount of product Type (g/kg·hr) | Selectivity Type (%) | |
| 11 | 4.2 | MPC (99) | Pb(OPh)$_2$ (8.0) | 195 | 194 | 2.1 | 1.0 | 3.2 | DPC (75.7) | DPC (757) | DPC (99) | |
| 12 | 4.2 | MPC (99) | Bu$_2$SnO (12.8) | 194 | 199 | 2.0 | 1.2 | 3.0 | DPC (73.8) | DPC (738) | DPC (99) | |
| 13 | 4.0 | EPC (99) | Pb(OPh)$_2$ (10.5) | 198 | 241 | 2.3 | 1.1 | 2.9 | DPC (70.9) | DPC (709) | DPC (99) | |
| 14 | 4.3 | MTC (99) | Pb(OPh)$_2$ (12.0) | 201 | 182 | 1.7 | 1.4 | 2.9 | DTC (77.3) | DTC (773) | DTC (99) | |
| 15 | 4.2 | MPC (99) | Ti(OPh)$_4$ (12.5) | 195 | 223 | 1.8 | 1.2 | 3.0 | DPC (70.5) | DPC (705) | DPC (99) | |
| 16 | 6.3 | MPC (85) PhOH (14) | Pb(OPh)$_2$ (10.5) | 195 | 270 | 2.1 | 1.9 | 4.4 | DPC (61.8) | DPC (618) | DPC (99) | |
| 17 | 4.2 | MPC (99) | Pb(OPh)$_2$ (40.0) | 194 | 91 | 2.1 | 1.4 | 3.4 | DPC (91.2) | DPC (912) | DPC (99) | |

<Description of symbols>
Pb(OPh)$_2$: diphenoxy lead
Bu$_2$SnO: dibutyl tin oxide
Ti(OPh)$_4$: tetraphenoxy titanium
MPC: methyl phenyl carbonate
MTC: methyl tolyl carbonate
EPC: ethyl phenyl carbonate
DPC: diphenyl carbonate
DTC: ditolyl carbonate
wt %: % by weight
(Note)
1. The catalyst concentration was determined by means of an ICP (inductively coupled plasma emission spectral analyzer).
2. The amount of the produced diaryl carbonate is expressed in terms of grams of the product per kg of the column bottom liquid and per hour.
3. The selectivity of the diaryl carbonate is calculate, based on the alkyl aryl carbonate, a raw material, converted.

TABLE 4

| Example | Feed liquid from feeding pipe 2 | | | Feed liquid from feeding pipe 8' | | Reaction conditions | | Condensate (conduit 16) Flow rate kg/hr | Column bottom liquid (conduit 19) | | Diaryl carbonate | |
|---|---|---|---|---|---|---|---|---|---|---|---|---|
|  | Flow rate kg/hr | Alkyl aryl carbonate Type (wt %) | Catalyst Type (mmol/kg) | Flow rate (kg/hr) | Composition Type | Temperature at column bottom °C. | Pressure at column top mmHg |  | Flow rate kg/hr | Composition Type (wt %) | Amount of product Type (g/kg·hr) | Selectivity Type (%) |
| 18 | 4.2 | MPC (99) | Pb(OPh)$_2$ (8.0) | 4.5 | MPC | 192 | 321 | 3.2 | 5.5 | DPC (46.8) | DPC (468) | DPC (99) |
| 19 | 4.2 | MPC (99) | Bu$_2$SnO (12.8) | 1.3 | PhOH | 190 | 274 | 3.7 | 5.0 | DPC (52.3) | DPC (523) | DPC (99) |
| 20 | 4.0 | MPC (99) | Pb(OPh)$_2$ (10.5) | 2.0 | MPC | 191 | 289 | 2.8 | 5.2 | DPC (50.4) | DPC (504) | DPC (99) |
| 21 | 34.5 | MPC | Pb(OPh)$_2$ | 37.0 | MPC | 190 | 275 | 28.0 | 43.5 | DPC | DPC | DPC |

TABLE 4-continued

| | Feed liquid from feeding pipe 2 | | | Feed liquid from feeding pipe 8' | | Reaction conditions | | Condensate (conduit 16) Flow rate kg/hr | Column bottom liquid (conduit 19) | | Diaryl carbonate | |
|---|---|---|---|---|---|---|---|---|---|---|---|---|
| | | Composition | | | | Temperature at column bottom °C. | Pressure at column top mmHg | | | | | |
| Example | Flow rate kg/hr | Alkyl aryl carbonate Type (wt %) | Catalyst Type (mmol/kg) | Flow rate (kg/hr) | Composition Type | | | | Flow rate kg/hr | Composition Type (wt %) | Amount of product Type (g/kg · hr) | Selectivity Type (%) |
| | | (99) | (13.5) | | | | | | | (52.5) | (525) | (99) |

<Description of symbols>
PhOH: phenol
Pb(OPh)$_2$: diphenoxy lead
Bu$_2$SnO: dibutyl tin oxide
MPC: methyl phenyl carbonate
DPC: diphenyl carbonate
wt %: % by weight
(Note)
1. The catalyst concentration was determined by means of an ICP (inductively coupled plasma emission spectral analyzer).
2. The amount of the produced diaryl carbonate is expressed in terms of grams of the product per kg of the column bottom liquid and per hour.
3. The selectivity of the diaryl carbonate is calculated, based on the alkyl aryl carbonate, a raw material, converted.

TABLE 5

First continuous multi-stage distillation column

| Example | Feed liquid from feeding pipe 2 | | Feed liquid from feeding pipe 6 | | Feed liquid from feeding pipe 8' | | Reaction conditions | | | Condensate (conduit 16) Flow rate kg/hr | Column bottom liquid (conduit 19) | |
|---|---|---|---|---|---|---|---|---|---|---|---|---|
| | Flow rate kg/hr | Composition wt % | Flow rate kg/hr | Composition wt % | Flow rate kg/hr | Composition wt % | Temperature at column bottom °C. | Pressure at column top kg/cm$^2$-G | Reflux ratio | | Flow rate kg/hr | Composition wt % |
| 22 | 2.7 | DMC (81.1) PhOH (17.0) Pb (0.95) | 6.4 | DMC (72.4) PhOH (26.5) MPC (0.4) Pb (0.38) | — | — (—) | 203 | 6.5 | 1.5 | 2.2 | 4.1 | MPC (10.9) |
| 23 | 2.7 | DMC (79.9) PhOH (18.3) Sn (0.91) | 6.4 | DMC (68.5) PhOH (30.4) MPC (0.4) Sn (0.37) | — | — (—) | 202 | 6.5 | 1.5 | 2.2 | 4.1 | MPC (8.3) |
| 24 | 0.9 | DMC (3.8) PhOH (92.8) Pb (1.8) | 4.6 | DMC (50.6) PhOH (45.3) MPC (3.3) Pb (0.37) | 3.0 | DMC (100) | 204 | 8 | 0 | 3.1 | 4.5 | MPC (27.4) |
| 25 | 2.0 | DMC (37.0) COH (61.4) Pb (0.84) | 5.8 | DMC (54.3) COH (42.5) MTC (2.6) Pb (0.32) | 2.3 | DMC (100) | 204 | 6 | 0 | 3.3 | 4.8 | MTC (30.8) |
| 26 | 0.68 | DEC (10.8) PhOH (84.4) Pb (2.6) | 5.3 | DEC (66.3) PhOH (30.0) EPC (3.1) Pb (0.32) | 3.0 | DEC (90.9) PhOH (9.1) | 202 | 4 | 0 | 2.9 | 5.4 | EPC (23.1) |
| 27 | 0.95 | DMC (26.4) PhOH (71.5) Sn (2.0) | 4.5 | DMC (50.4) PhOH (46.1) MPC (3.1) Sn (0.38) | 3.1 | DMC (90.5) PhOH (9.5) | 203 | 6 | 0 | 3.2 | 4.4 | MPC (24.1) |

TABLE 5-continued

| | | | | | | | | | | | | |
|---|---|---|---|---|---|---|---|---|---|---|---|---|
| 28 | 0.99 | DMC (31.5) PhOH (65.2) Ti (1.9) | 4.6 | DMC (49.3) PhOH (44.8) MPC (5.3) Ti (0.40) | 3.2 | DMC (91.3) PhOH (8.7) | 204 | 6 | 0 | 3.4 | 4.4 | MPC (26.9) |
| 30 | 0.11 | DMC (41.8) PhOH (58.2) | 1.1 | DMC (51.3) PhOH (45.6) MPC (3.0) | 0.78 | DMC (90.3) PhOH (9.7) | 203 | 6 | 0 | 0.75 | 1.1 | MPC (18.1) |

| | Second continuous multi-stage distillation column | | | | Column bottom liquid (conduit 28) | | Diaryl carbonate | |
|---|---|---|---|---|---|---|---|---|
| | Reaction conditions | | | Condensate (conduit 25) | Flow rate kg/hr | | Amount of product | Selectivity |
| Example | Temperature at column bottom °C | Pressure at column top mmHg | Reflux ratio | Flow rate kg/hr | | Composition wt % | Type g/kg Hr | Type (%) |
| 22 | 198 | 300 | 1.6 | 3.7 | 0.35 | DPC (82.8) | DPC (828) | DPC (98) |
| 23 | 197 | 300 | 1.6 | 3.7 | 0.35 | DPC (52.4) | DPC (524) | DPC (95) |
| 24 | 195 | 310 | 1.5 | 3.7 | 0.81 | DPC (92.6) | DPC (926) | DPC (98) |
| 25 | 196 | 200 | 1.8 | 3.8 | 1.0 | DTC (90.2) | DTC (902) | DTC (98) |
| 26 | 198 | 220 | 2.1 | 4.7 | 0.78 | DPC (85.4) | DPC (854) | DPC (98) |
| 27 | 199 | 560 | 1.7 | 3.5 | 0.85 | DPC (62.5) | DPC (625) | DPC (95) |
| 28 | 197 | 560 | 1.5 | 3.6 | 0.79 | DPC (74.3) | DPC (743) | DPC (95) |
| 30 | 198 | 560 | 1.0 | 1.0 | 0.13 | DPC (66.2) | DPC (662) | DPC (95) |

[Description of symbols]
DMC: dimethyl carbonate
PhOH: phenol
Pb: lead
MPC: methyl phenyl carbonate
DPC: diphenyl carbonate
COH: p-cresol
MTC: methyl tolyl carbonate
DTC: ditolyl carbonate
DEC: diethyl carbonate
EPC: ethyl phenyl carbonate
Sn: tin
Ti: titanium
wt %: % by weight
(Note)
1. The catalyst concentration was determined by means of an ICP (inductively coupled plasma emission spectral analyzer). The catalyst concentration is expressed in terms of the concentration (% by weight) of a catalyst element in the liquid.
2. The amount of produced diaryl carbonate is expressed in terms of grams of the product per kg of the column bottom liquid (conduit 28) and per hour.
3. The selectivity of the diaryl carbonate is calculated by means of the following formula. Selectivity of the diaryl carbonate (%) = [selectivity (%) at Step 1 based on the aromatic hydroxy compound converted] × [selectivity (%) at Step 2 based on the alkyl aryl carbonate converted] ÷ 100

TABLE 6

| First continuous multi-stage distillation column | | | | | | | | | |
|---|---|---|---|---|---|---|---|---|---|
| Feeding pipe 2 | | Conduit 6 | | Feeding pipe 8' | | Conduit 16 | Conduit 19 | | |
| Flow rate (kg/Hr) | Composition Type (wt %) | Flow rate (kg/Hr) | Composition Type (wt %) | Flow rate (kg/Hr) | Composition Type (wt %) | Flow rate (kg/Hr) | Flow rate (kg/Hr) | Composition Type (wt %) | |
| 5.0 | DMC (13.1) PhOH (86.9) | 24.5 | DMC (51.2) PhOH (43.3) MPC (4.7) Pb (0.42) | 41.5 | DMC (89.5) PhOH (10.5) | 42.4 | 23.6 | MPC (28.9) | |

| First evaporator | | Second continuous multi-stage distillation column | | | | | Second evaporator | | |
|---|---|---|---|---|---|---|---|---|---|
| Conduit 40 | Conduit 38 | Conduit 41 | | Conduit 25 | Conduit 32 | | Conduit 50 | | Conduit 47 |
| Flow rate (kg/Hr) | Flow rate (kg/Hr) | Flow rate (kg/Hr) | Composition Type (wt %) | Flow rate (kg/Hr) | Flow rate (kg/Hr) | Composition Type (wt %) | Flow rate (kg/Hr) | Composition Type (wt %) | Flow rate (kg/Hr) |
| 22.3 | 1.3 | 23.3 | DMC (43.1) PhOH (24.5) MPC (27.1) DPC (4.5) | 18.3 | 5.3 | DPC (95.4) | 4.0 | DPC (98.3) | 1.2 |

TABLE 6-continued

Pb (0.8)

<Description of symbols>
DMC: dimethyl carbonate
PhOH: phenol
Pb: lead
MPC: methyl phenyl carbonate
DPC: diphenyl carbonate
wt %: % by weight
(Note)
The catalyst concentration is expressed in terms of the Pb concentration (wt %) in the liquid measured by means of an ICP (inductively coupled plasma emission spectral analyzer).

TABLE 7

| First continuous multi-stage distillation column Reaction conditions | | | Second continuous multi-stage distillation column Reaction conditions | | | Reaction results Diaryl carbonate | |
| --- | --- | --- | --- | --- | --- | --- | --- |
| Temperature at column bottom (°C.) | Pressure at column top (kg/cm² − G) | Reflux ratio | Temperature at column bottom (°C.) | Pressure at column top (mmHg) | Reflux ratio | Amount of product Type (g/kg · Hr) | Selectivity Type (%) |
| 203 | 6.5 | 0 | 198 | 280 | 1.5 | DPC (983) | DPC (98) |

<Description of symbols>
DPC: diphenyl carbonate
wt %: % by weight
(Note)
The amount of the produced diaryl carbonate is expressed in terms of grams of the product per kg of withdrawn liquid from conduit 50 and per hour.
The selectivity of the diaryl carbonate is calculated by means of the following formula.
Selectivity of the diaryl carbonate (%) = [selectivity (%) at Step 1 based on the aromatic hydroxy compound converted] × [selectivity (%) at Step 2 based on the alkyl aryl carbonate converted] ÷ 100

EXAMPLE 31

Using a distillation column as shown in FIG. 2 as the first continuous multi-stage distillation column, a mixture of dimethyl carbonate, para-cresol and Pb(OPh)$_2$ [46% by weight of dimethyl carbonate, 54% by weight of para-cresol, and 10 mmol/kg of Pb(OPh)$_2$] was continuously fed at 7.0 kg/hr from feeding pipe 2 through preheater 5, and simultaneously, dimethyl carbonate was continuously fed at 2.8 kg/hr from feeding pipe 8' through evaporator 10' and conduit 11, thereby effecting reaction at a temperature at column bottom of 205° C. and at a pressure at column top of 6 kg/cm$^2$-G, while continuously withdrawing as a condensate a gas component containing methanol at 5.0 kg/hr from column top 17 through conduit 12 and condenser 13, and on the other hand, continuously withdrawing a column bottom liquid containing 30% by weight of methyl tolyl carbonate at 4.8 kg/hr from the column bottom through conduit 19.

Substantially the same operation was performed using diethyl carbonate, phenol and Pb(OPh)$_2$, to thereby obtain a column bottom liquid containing 28.8% weight of ethyl phenyl carbonate.

A distillation column as shown in FIG. 1 was used as the second continuous multi-stage distillation column, and the column bottom liquid from the first continuous multi-stage distillation column was continuously fed to the second continuous multi-stage distillation column at 4.8 kg/hr from feeding pipe 2 through preheater 5 and conduit 6. Simultaneously, the above-mentioned column bottom liquid containing ethyl phenyl carbonate was continuously fed at 5.0 kg/hr from the same feeding pipe 2. The temperature at the bottom of the second continuous multi-stage distillation column was 200° C., and the pressure at column top 17 was 200 mmHg. A gas component containing dimethyl carbonate, diethyl carbonate and methyl ethyl carbonate was continuously withdrawn as a condensate at 7.7 kg/hr from column top 17 through conduit 12, condenser 13 and conduits 14 and 16. On the other hand, the column bottom liquid was continuously withdrawn at 2.1 kg/hr through conduits 8 and 19. 88% by weight of the column bottom liquid was diaryl carbonate comprising diphenyl carbonate, ditolyl carbonate and phenyl tolyl carbonate, and the proportions of diphenyl carbonate:ditolyl carbonate:phenyl tolyl carbonate were about 1:1:0.8.

EXAMPLE 32

By substantially the same operation as that employed with the first continuous multi-stage distillation column in Example 25, a column bottom liquid containing methyl tolyl carbonate was continuously withdrawn at 4.8 kg/hr from dimethyl carbonate and para-cresol, and the withdrawn liquid was continuously fed to the second continuous multi-stage distillation column while methyl phenyl carbonate was continuously fed to the second continuous multi-stage distillation column at 1.36 kg/hr through conduit 19. The reaction conditions in the second continuous multi-stage column were substantially the same as those of Example 25. From the time when methyl phenyl carbonate was added, the amount of dimethyl carbonate in the feed liquid fed from feeding pipe 2 was gradually decreased so as to obtain a rate of 0.38 kg/hr. Instead, the amount of dimethyl carbonate in the feed liquid from conduit 6 was increased by 0.36 kg/hr. The increase was due to the fact that the reaction in the second continuous multi-stage distillation column, in which transesterification occurred between methyl tolyl carbonate and methyl phenyl carbonate, caused an increase in the amount of the dimethyl carbonate formed as a low boiling point by-product.

On the other hand, the column bottom liquid containing 90% by weight of diaryl carbonate comprised of diphenyl carbonate, ditolyl carbonate and phenyl tolyl carbonate was continuously withdrawn at 2 kg/hr from the bottom of the second continuous multi-stage distillation column. The proportions in the diaryl carbonate of diphenyl carbonate:ditolyl carbonate:phenyl tolyl carbonate were about 1:1:0.75.

Industrial Applicability

The process of the present invention in which a continuous multi-stage distillation column is used to continuously produce an aromatic carbonate at a high reaction rate, with a high selectivity and in a high yield, can be advantageously utilized in the mass production of an aromatic carbonate, which is useful as a material for the production of aromatic polycarbonates, whose utility as engineering plastics is increasing in recent years, without using poisonous phosgene or as a material for the production of various isocyanates without using poisonous phosgene.

We claim:

1. In a process for producing an aromatic carbonate which comprises transesterifying a starting material selected from the group consisting of a dialkyl carbonate represented by

an alkyl aryl carbonate represented by

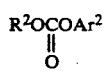

and a mixture thereof with a reactant selected from the group consisting of an aromatic hydroxy compound represented by $Ar^1OH$, an alkyl aryl carbonate represented by

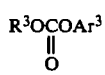

and a mixture thereof, wherein each of $R^1$, $R^2$ and $R^3$ independently represents an alkyl group having 1 to 10 carbon atoms, an alicyclic group having 3 to 10 carbon atoms or an aralkyl group having 6 to 10 carbon atoms and each of $Ar^1$, $Ar^2$ and $Ar^3$ independently represents an aromatic group having 5 to 30 carbon atoms, to thereby produce an aromatic carbonate or aromatic carbonate mixture corresponding to the starting material and the reactant and represented by

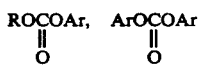

or a mixture thereof, wherein R and Ar are, respectively, selected from $R^1$, $R^2$ and $R^3$ and selected from $Ar^1$, $Ar^2$ and $Ar^3$ in correspondence to the starting material and the reactant and produce an aliphatic alcohol, a dialkyl carbonate or a mixture thereof corresponding to the starting material and the reactant and represented by ROH,

or a mixture thereof, wherein R is as defined above as a by-product, with the proviso that when R is $R^2$, Ar is not $Ar^2$, the improvement in which said starting material and said reactant are continuously fed to a continuous multi-stage distillation column to effect transesterification reaction therebetween in at least one phase selected from a liquid phase and a gas-liquid phase in the presence of a catalyst in said distillation column, while continuously withdrawing a high boiling point reaction mixture containing the produced aromatic carbonate or aromatic carbonate mixture in a liquid form from a lower portion of the distillation column and continuously withdrawing a low boiling point reaction mixture containing the by-product in a gaseous form from an upper portion of the distillation column by distillation, thereby enabling the aromatic carbonate or aromatic carbonate mixture to be produced continuously.

2. The process according to claim 1, wherein said catalyst is a catalyst which is soluble in said liquid phase, and is present in a state dissolved in said liquid phase within the continuous multi-stage distillation column, and/or wherein said catalyst is a solid catalyst which is substantially insoluble in said liquid phase, and is disposed, in a state undissolved in said liquid phase, within the continuous multi-stage distillation column.

3. The process according to claim 1, wherein said continuous multi-stage distillation column is used as a first continuous multi-stage distillation column and has a second continuous multi-stage distillation column connected thereto and wherein the starting material and the reactant which are continuously fed to the first continuous multi-stage distillation column are, respectively, a dialkyl carbonate represented by

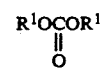

and an aromatic hydroxy compound represented by $Ar^1OH$, the aromatic carbonate or aromatic carbonate mixture contained in the produced high boiling point reaction mixture continuously withdrawn from the lower portion of the first distillation column is an alkyl aryl carbonate represented by

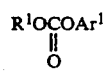

in which $R^1$ and $Ar^1$ are as defined above, and the by-product contained in the produced low boiling point reaction mixture continuously withdrawn from the upper portion of the first distillation column is an aliphatic alcohol represented by $R^1OH$, and which process further comprises continuously feeding the produced high boiling point reaction mixture continuously withdrawn from the lower portion of the first distillation column and containing the alkyl aryl carbonate represented by

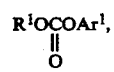

in which $R^1$ and $Ar^1$ are as defined above, and an alkyl aryl carbonate reactant represented by

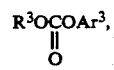

in which $R^3$ is the same as or different from $R^1$ and $Ar^3$ is the same as or different from $Ar^1$ with the proviso that $R^3$ and $Ar^3$ are, respectively, not simultaneously the same as $R^1$ and $Ar^1$, to the second continuous multi-stage distillation column to effect transesterification reaction therebetween in at least one phase selected from a liquid phase and a gas-liquid phase in the presence of a catalyst in said second distillation column, thereby producing a high boiling point reaction mixture containing a diaryl carbonate or diaryl carbonate mixture represented by

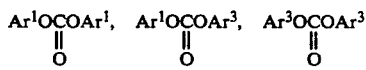

or a mixture thereof, in which $Ar^1$ and $Ar^3$ are as defined above, and a low boiling point reaction mixture containing a dialkyl carbonate by-product represented by

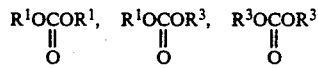

or a mixture thereof, in which $R^1$ and $R^3$ are as defined above, wherein the produced high boiling point reaction mixture is continuously withdrawn in a liquid form from a lower portion of said second distillation column and the low boiling point reaction mixture is continuously withdrawn in a gaseous form from an upper portion of said second distillation column by distillation.

4. The process according to claim 3, wherein said catalyst is a catalyst which is soluble in said liquid phase, and is present in a state dissolved in said liquid phase within at least one of the first continuous multi-stage distillation column and the second continuous multi-stage distillation column, or wherein said catalyst is a solid catalyst which is substantially insoluble in said liquid phase, and is in a dispersed state undissolved in said liquid phase, within at least one of the first continuous multi-stage distillation column and the second continuous multi-stage distillation column.

5. The process according to claim 3, wherein $R^3$ is the same as $R^1$ and $Ar^3$ is different from $Ar^1$, and which process further comprises recycling the low boiling point reaction mixture withdrawn from the upper portion of the second continuous multi-stage distillation column and containing a dialkyl carbonate represented by

to the first continuous multi-stage distillation column.

6. The process according to claim 1, wherein said continuous multi-stage distillation column is used as a first continuous multi-stage distillation column and has a second continuous multi-stage distillation column connected thereto and wherein the starting material and the reactant which are continuously fed to the first continuous multi-stage distillation column are, respectively, a dialkyl carbonate represented by

an aromatic hydroxy compound represented by $Ar^1OH$, the aromatic carbonate or aromatic carbonate mixture contained in the produced high boiling point reaction mixture continuously withdrawn from the lower portion of the first distillation column is an alkyl aryl carbonate represented by

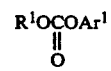

in which $R^1$ and $Ar^1$ are as defined above, and the by-product contained in the produced low boiling point reaction mixture continuously withdrawn from the upper portion of the first distillation column is an aliphatic alcohol represented by $R^1OH$, and which process further comprises continuously feeding the produced high boiling point reaction mixture continuously withdrawn from the lower portion of the first distillation column and containing the alkyl aryl carbonate represented by

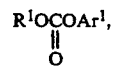

in which $R^1$ and $Ar^1$ are as defined above, to the second continuous multi-stage distillation column to effect a same species-intermolecular transesterification reaction in at least one phase selected form a liquid phase and a gas-liquid phase between molecules of the alkyl aryl carbonate in the presence of a catalyst in said second distillation column, thereby producing a high boiling point reaction mixture containing a diaryl carbonate represented by

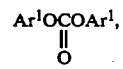

in which $Ar^1$ is as defined above, and a low boiling point reaction mixture containing a dialkyl carbonate by-product represented by

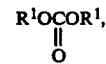

in which $R^1$ is as defined above, wherein the produced high boiling point reaction mixture is continuously withdrawn in a liquid form from a lower portion of said second continuous multi-stage distillation column and the lower boiling point reaction mixture is continuously withdrawn in a gaseous form from an upper portion of said second continuous multi-stage distillation column.

7. The process according to claim 6, which further comprises recycling the low boiling point reaction mixture withdrawn from the upper portion of said second continuous multi-stage distillation column and containing the dialkyl carbonate represented by

to said first continuous multi-stage distillation column.

8. The process according to claim 6 or 7, wherein said catalyst is a catalyst which is soluble in said liquid phase, and is present in a state dissolved in said liquid phase within at least one of the first continuous multi-stage distillation column and the second continuous multi-stage distillation column, or wherein said catalyst is a solid catalyst which is substantially insoluble in said liquid phase, and is in a dispersed state undissolved in said liquid phase, within at least one of the first continuous multi-stage distillation column and the second continuous multi-stage distillation column.

9. The process according to claim 8, wherein said catalyst is a catalyst which is soluble in said liquid phase, and is present in a state dissolved in said liquid phase within each of the first continuous multi-stage distillation column and the second continuous multi-stage distillation column, wherein the respective catalysts used in the first and second distillation columns are the same or different.

10. The process according to claim 6 or 7, wherein part or all of the catalyst used in the first continuous multi-stage distillation column is present in a state dissolved in said liquid phase and wherein, in feeding to the second continuous multi-stage distillation column the high boiling point reaction mixture withdrawn in liquid form from the lower portion of the first distillation column, the withdrawn high boiling point reaction mixture in liquid form is introduced to a first evaporator to effect a separation of said reaction mixture into an evaporated component containing the alkyl aryl carbonate represented by

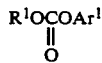

and a residual liquid having the catalyst dissolved therein, and part or all of said evaporated component is fed to the second continuous multi-stage distillation column, while recycling part or all of the residual liquid containing the dissolved catalyst to the first continuous multi-stage distillation column.

11. The process according to claim 6 or 7, wherein part or all of the catalyst used in the second continuous multi-stage distillation column is present in a state dissolved in said liquid phase, and which process further comprises introducing the high boiling point reaction mixture withdrawn in liquid form from the lower portion of the second distillation column to a second evaporator to effect a separation of said reaction mixture into an evaporated component containing a diaryl carbonate represented by

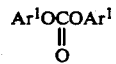

and a residual liquid having said catalyst dissolved therein, and recycling part or all of the residual liquid containing the dissolved catalyst to the second continuous multi-stage distillation column.

12. The process according to claim 10, wherein part or all of the catalyst used in the second continuous multi-stage distillation column is present in a state dissolved in said liquid phase, and which process further comprises introducing the high boiling point reaction mixture withdrawn in liquid form from the lower portion of the second distillation column to a second evaporator to effect a separation of said reaction mixture into an evaporated component containing a diaryl carbonate represented by

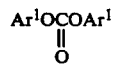

and a residual liquid having said catalyst dissolved therein, and recycling part or all of the residual liquid containing the dissolved catalyst to the second continuous multi-stage distillation column.

13. The process according to any one of claims 1 to 7, wherein said catalyst is selected from the group consisting of a lead compound, a copper family metal compound, an alkali metal complex, a zinc complex, a cadmium complex, an iron family metal compound, a zirconium complex, a Lewis acid or Lewis acid-forming compound, an organotin compound and an inorganic oxide.

14. The process according to claim 8, wherein said catalyst is selected from the group consisting of a lead compound, a copper family metal compound, an alkali metal complex, a zinc complex, a cadmium complex, an iron family metal compound, a zirconium complex, a Lewis acid or Lewis acid-forming compound, an organotin compound and an inorganic oxide.

15. The process according to claim 1 or 2, wherein said continuous multi-stage distillation column is of a plate column type, a packed column type or a mixed type of plate column and packed column.

16. The process according to any one of claims 3 to 7, wherein each of said first continuous multi-stage distillation column and said second continuous multi-stage distillation column is, independently, of a plate column type, a packed column type or a mixed type of plate column and packed column.

* * * * *